(12) United States Patent
Georgiou et al.

(10) Patent No.: US 7,419,783 B2
(45) Date of Patent: Sep. 2, 2008

(54) ENGINEERING OF LEADER PEPTIDES FOR THE SECRETION OF RECOMBINANT PROTEINS IN BACTERIA

(75) Inventors: George Georgiou, Austin, TX (US); Matthew DeLisa, Austin, TX (US)

(73) Assignee: Research Development Foundation, Carson City, NV (US)

( * ) Notice: Subject to any disclaimer, the term of this patent is extended or adjusted under 35 U.S.C. 154(b) by 635 days.

(21) Appl. No.: 10/289,135

(22) Filed: Nov. 5, 2002

(65) Prior Publication Data

US 2003/0180937 A1 Sep. 25, 2003

Related U.S. Application Data

(60) Provisional application No. 60/404,994, filed on Aug. 21, 2002, provisional application No. 60/337,452, filed on Nov. 5, 2001.

(51) Int. Cl.
*C12Q 1/68* (2006.01)
*C12P 21/00* (2006.01)
*C07H 21/04* (2006.01)
*C07K 14/00* (2006.01)
*C07K 14/195* (2006.01)

(52) U.S. Cl. .................... 435/6; 435/69.1; 536/23.1; 530/324

(58) Field of Classification Search ............... 435/6, 435/69.1; 536/23.1
See application file for complete search history.

(56) References Cited

U.S. PATENT DOCUMENTS

2002/0110860 A1   8/2002   Bron et al.
2002/0182672 A1   12/2002   Kolkman

FOREIGN PATENT DOCUMENTS

| WO | WO 99/45136 | 9/1999 |
| WO | WO 99/51753 | 10/1999 |
| WO | WO 02/22667 | 3/2002 |
| WO | WO 02/055717 | 7/2002 |

OTHER PUBLICATIONS

Chen et al. Isoaltion of high-affinity ligand-binding proteins by periplasmic expression with cytomethric screening (PECS) Nature Biotechnology vol. 19 Jun. 2001 pp. 537-542.*
Feilmeier et al. Green Fleuroescent Protein Functions as a Report for Protein Localization in *E. coli* J. Bacteriology vol. 182 No. 14 Jul. 200 pp. 4068-4076.*
Berks et al. The Tat Protein Export Pathway Mol. Microbio. vol. 35 No. 2 Jan. 2000 p. 260.*
Berks et al., "The Tat protein export pathway," *Mol. Microbiol.*, 35:260-274, 2000.
Berks, "A common export pathyway for proteins binding complex redox cofactors," *Mol. Microbiol.*, 22:393-404, 1996.

Bessette et al., "Efficient folding of proteins with multiple disulfide bonds in the *Escherichia coli* cytoplasm," *Proc. Natl. Acad. Sci., USA*, 96:13703-13708, 1999.
Bowden and Georgiou, "Folding and aggregation of β-lactamase in the periplasmic space of *Escherichia coli*,"*J. Biol. Chem.*, 265:16760-16766, 1990.
Crameri et al., "Improved green fluorescent protein by molecular evolution using dna shuffling," *Nat. Biotechnol.*, 14:315-319, 1996.
Cristobal et al., "Competition between Sec- and TAT-dependent protein translocation in *Escherichia coli*," *EMBO J.*, 18:2982-2990, 1999.
Danese and Silhavy, "Targeting and assembly of periplasmic and outer-membrane proteins in *Escherichia coli*," *Annu. Rev. Genet.*, 32:59-94, 1998.
DeLisa et al., "Genetic analysis of the twin arginine translocator secretion pathway in bacteria," *J. Biol. Chem.*, 277(33):29825-29831, 2002.
Feilmeier et al., "Green fluorescent protein functions as a reporter for protein localization in *Escherichia coli*, " *J. Bacteriol.*, 182:4068-4076, 2000.
Georgiou and Valax, "Expression of correctly folded proteins in *Escherichia coli*, " *Curr. Opin. Biotechnol.*, 7(2):190-197, 1996.
Guzman et al., "Tight regulation, modulation, and high-level expression by vectors containing the Arabinose $P_{BAD}$ promoter," *J. Bacteriol.*, 177:4121-4130, 1995.
Karzai et al., "The SssrA-SmpB system for protein tagging, directed degradation and ribosome rescue,"*Nat. Struct. Biol.*, 7:449-455, 2000.
Pugsley, "The compolete general secretary pathway in gram-negative bacteria," *Microbiol. Rev.*, 57:50-108, 1993.
Santini et al., "Translocation of jellyfish green fluorescent protein via the Tat system of *Escherichia coli* and change of its periplasmic localization in response to osmotic up-shock," *J. Biol. Chem.*, 276:8159-8164, 2001.

(Continued)

*Primary Examiner*—Michael Burkhart
(74) *Attorney, Agent, or Firm*—Fulbright & Jaworski L.L.P.

(57) ABSTRACT

The present invention provides methods of isolating of leader peptides capable of directing export of heterologous proteins from the bacterial cytoplasm. The methods rely on the screening of libraries of putative leader peptides or of leader peptide mutants for sequences that allow rapid export and thus can rescue a short-lived reporter protein from degradation in the cytoplasm. The mutant leader peptides identified herein are shown to confer significantly higher steady state levels of export not only for short-lived reporter protein but also for other stable, long-lived proteins. These leader peptides can be used to direct or enhance protein secretion. The present invention further discloses methods for the export of cytoplasmically folded protein via the Tat pathway. Proteins having disulfide bonds are first folded within the cytoplasm in suitable oxidizing mutant strains. Such cytoplasmically prefolded proteins containing disulfide bonds are then exported via the Tat pathway.

20 Claims, 7 Drawing Sheets

OTHER PUBLICATIONS

Thomas et al., "Export of active green fluorescent protein to the periplasm by the twin-arginine translocase (Tat) pathway in *Escherichia coli*," *Mol. Microbiol.*, 39:47-53, 2001.

Better et al., "*Escherichia coli* secretion of an active chimeric antibody fragment," *Science*, 240:1041-1043, 1988.

Daugherty et al., "Quantitative analysis of the effect of the maturation frequency on the affinity maturation of single chain Fv antibodies," *Proc. Natl. Acad. Sci., USA*, 97(5):2000.

Buchner and Rudolph, "Renaturation, purification, and characterization of recombinant Fab-fragments produced in *Escherichia coli*," *Enzyme Microb. Technol.*, 9(2):157-162, 1991.

Delisa et al., "Folding quality control in the export of proteins by the bacterial twin-arginine translocation pathway in bacteria," *Proceedings of the National Academy of Sciences*, 10:6115-6120, 2003.

Kipriyanov et al., "Rapid detection of recombinant antibody fragments directed against cell surface antigens by flow cytometry," *J. Immunol. Methods*, 196(1):51-62, 1996.

Le and Trotta, "Purification of secreted recombinant proteins from *Escherichia coli*," *Bioprocess Technol.*, 12:163-181, 1991.

Makrides, "Strategies for achieving high-level expression of genes in *Escherichia coli*," *Microbiol. Rev.*, 60(3):512-538, 1996.

Wulfing and Pluckthun, "Protein folding in the periplasm of *Escherichia coli*," *Molecular Microbiology*, 12(5):685-692, 1994.

Andersen et al., "New unstable variants of 1-13 green fluorescent protein for studies of transient gene expression in bacteria", *Applied and Environmental Microbiology*, 6:2240-2246, 1998.

Berg et al., "Nitrate-inducible formate dehydrogenase in *escherichia-coli* k-12 I. Nucleotide sequence of the FDN GHI operon and evidence that opal UGA encodes selenocysteine", *Journal of Biological Chemistry*, 33:22380-22385, 1991.

Buchanan et al., "A genetic screen for suppressors of *escherichia coli* tat signal peptide mutations establishes a critical role for the second arginine within the twin-arginine motif", *Archives of Microbiology*, 177:107-112, 2001.

Hinsley et al., "A naturally occurring bacterial tat signal peptide lacking one of the 'invariant' arginine residues of the consensus targeting motif", *FEBS Letters*, 1:45-59, 2001.

Klein et al., "Effects of signal peptide changes on the secretion of bovine somatotropin (BST) from *escherichia coli*", *Protein Engineering*, 6: 511-517, 1992.

Matteucci et al., "Alkaline phosphatase fusions: a tag to identify mutations that result in increase expression of secreted human growth hormone from *e. coli*", *Bio/Technology*, 4: 51-55, 1986.

Blaudeck et al., "Specificity of signal peptide recognition in tat-dependent bacterial protein translocation," *J. Bact.*, 183:604-610, 2001.

Delisa et al., "Phage shock protein PspA of *Escherichia coli* relieves saturation of protein export via the fat pathway," *J. Bact.*, 186:366-373, 2004.

Ize et al., "In vivo dissection of the Tat translocation pathway in *Escherichia coli*," *J. Mol. Biol.*, 317:327-335, 2002.

\* cited by examiner

SEQUENCE LISTING

<160> NUMBER OF SEQ ID NOS: 134

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (3)
<223> OTHER INFORMATION: Xaa = anything

<400> SEQUENCE: 1

Arg Arg Xaa Phe Leu Lys
  1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 2

Ser Arg Arg Arg Phe Leu Lys
  1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (4)..(7)
<223> OTHER INFORMATION: Xaa = anything

<400> SEQUENCE: 3

Ser Arg Arg Xaa Phe Leu Xaa
  1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (4)..(7)
<223> OTHER INFORMATION: Xaa = anything

<400> SEQUENCE: 4

Thr Arg Arg Xaa Phe Leu Xaa
  1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic

```
                        Peptide
<220> FEATURE:
<221> NAME/KEY: MOD_RES
<222> LOCATION: (4)..(5)
<223> OTHER INFORMATION: Xaa = anything

<400> SEQUENCE: 5

Ser Arg Arg Xaa Xaa Leu Lys
 1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide
<220> FEATURE:
<221> NAME/KEY: MOD_RES
<222> LOCATION: (4)..(5)
<223> OTHER INFORMATION: Xaa = anything

<400> SEQUENCE: 6

Ser Arg Arg Xaa Xaa Leu Ala
 1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide
<220> FEATURE:
<221> NAME/KEY: MOD_RES
<222> LOCATION: (4)..(5)
<223> OTHER INFORMATION: Xaa = anything

<400> SEQUENCE: 7

Thr Arg Arg Xaa Xaa Leu Lys
 1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide
<220> FEATURE:
<221> NAME/KEY: MOD_RES
<222> LOCATION: (4)..(5)
<223> OTHER INFORMATION: Xaa = anything

<400> SEQUENCE: 8

Thr Arg Arg Xaa Xaa Leu Ala
 1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide
<220> FEATURE:
<221> NAME/KEY: MOD_RES
<222> LOCATION: (4)..(5)
<223> OTHER INFORMATION: Xaa = anything

<400> SEQUENCE: 9
```

```
Ser Arg Arg Xaa Xaa Leu Thr
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (4)..(5)
<223> OTHER INFORMATION: Xaa = anything

<400> SEQUENCE: 10

Ser Arg Arg Xaa Xaa Ile Lys
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (4)..(5)
<223> OTHER INFORMATION: Xaa = anything

<400> SEQUENCE: 11

Ser Arg Arg Xaa Xaa Ile Ala
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (4)..(7)
<223> OTHER INFORMATION: Xaa = anything

<400> SEQUENCE: 12

Ser Arg Arg Xaa Phe Ile Xaa
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (4)
<223> OTHER INFORMATION: Xaa = anything

<400> SEQUENCE: 13

Ser Arg Arg Xaa Phe Met Lys
1               5

<210> SEQ ID NO 14
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (4)
<223> OTHER INFORMATION: Xaa = anything

<400> SEQUENCE: 14

Ser Arg Arg Xaa Phe Val Lys
 1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (4)
<223> OTHER INFORMATION: Xaa = anything

<400> SEQUENCE: 15

Ser Arg Arg Xaa Phe Val Ala
 1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 16

Ser Arg Arg Gln Phe Leu Lys
 1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (3)
<223> OTHER INFORMATION: Xaa = anything

<400> SEQUENCE: 17

Arg Arg Xaa Phe Leu Ala
 1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (3)
<223> OTHER INFORMATION: Xaa = anything

<400> SEQUENCE: 18
```

```
Arg Arg Xaa Phe Leu Lys
  1               5

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 19
gcgatggagc tcttaaagag gagaaaggtc                                      30

<210> SEQ ID NO 20
<211> LENGTH: 12
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 20
gcgatgtcta ga                                                         12

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (4)
<223> OTHER INFORMATION: Xaa = anything

<400> SEQUENCE: 21

Ser Arg Arg Xaa Phe Met Lys
  1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (4)
<223> OTHER INFORMATION: Xaa = anything

<400> SEQUENCE: 22

Ser Arg Arg Xaa Phe Val Lys
  1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (4)
<223> OTHER INFORMATION: Xaa = anything
```

```
<400> SEQUENCE: 23

Ser Arg Arg Xaa Phe Val Ala
  1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 24

Ser Arg Arg Gln Phe Leu Lys
  1               5

<210> SEQ ID NO 25
<211> LENGTH: 29
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 25

Met Pro Phe Lys Lys Leu Ser Arg Arg Thr Phe Leu Thr Ala Ser Ser
  1               5                  10                  15

Ala Leu Ala Phe Leu His Thr Pro Phe Ala Arg Ala Leu
             20                  25

<210> SEQ ID NO 26
<211> LENGTH: 28
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 26

Met Thr Trp Ser Arg Arg Gln Phe Leu Thr Gly Val Gly Val Leu Ala
  1               5                  10                  15

Ala Val Ser Gly Thr Ala Gly Arg Val Val Ala Lys
             20                  25

<210> SEQ ID NO 27
<211> LENGTH: 34
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 27

Met Lys Glu Ser Asn Ser Arg Arg Glu Phe Leu Ser Gln Ser Gly Lys
  1               5                  10                  15

Met Val Thr Ala Ala Ala Leu Phe Gly Thr Ser Val Pro Leu Ala His
             20                  25                  30

Ala Ala

<210> SEQ ID NO 28
<211> LENGTH: 46
<212> TYPE: PRT
<213> ORGANISM: Artificial Sequence
<220> FEATURE:
<223> OTHER INFORMATION: Description of Artificial Sequence: Synthetic
```

Peptide

<400> SEQUENCE: 28

Met Asn Asn Glu Glu Thr Phe Tyr Gln Ala Met Arg Arg Gln Gly Val
1               5                  10                  15

Thr Arg Arg Ser Phe Leu Lys Tyr Cys Ser Leu Ala Ala Thr Ser Leu
            20                  25                  30

Gly Leu Gly Ala Gly Met Ala Pro Lys Ile Ala Trp Ala Leu
        35                  40                  45

<210> SEQ ID NO 29
<211> LENGTH: 29
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 29

Met Gln Arg Arg Asp Phe Leu Lys Tyr Ser Val Ala Leu Gly Val Ala
1               5                  10                  15

Ser Ala Leu Pro Leu Trp Ser Arg Ala Val Phe Ala Ala
            20                  25

<210> SEQ ID NO 30
<211> LENGTH: 31
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 30

Met Asp Lys Phe Asp Ala Asn Arg Arg Lys Leu Leu Ala Leu Gly Gly
1               5                  10                  15

Val Ala Leu Gly Ala Ala Ile Leu Pro Thr Pro Ala Phe Ala Thr
            20                  25                  30

<210> SEQ ID NO 31
<211> LENGTH: 32
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 31

Met Arg His Ile Phe Gln Arg Leu Leu Pro Arg Arg Leu Trp Leu Ala
1               5                  10                  15

Gly Leu Pro Cys Leu Ala Leu Leu Gly Cys Val Gln Asn His Asn Lys
            20                  25                  30

<210> SEQ ID NO 32
<211> LENGTH: 36
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 32

Met Gln Tyr Lys Asp Glu Asn Gly Val Asn Glu Pro Ser Arg Arg Arg
1               5                  10                  15

Leu Leu Lys Val Ile Gly Ala Leu Ala Leu Ala Gly Ser Cys Pro Val

-continued

```
                20                  25                  30

Ala His Ala Gln
        35

<210> SEQ ID NO 33
<211> LENGTH: 35
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 33

Met Ser Thr Phe Lys Pro Leu Lys Thr Leu Thr Ser Arg Arg Gln Val
 1               5                  10                  15

Leu Lys Ala Gly Leu Ala Ala Leu Thr Leu Ser Gly Met Ser Gln Ala
                20                  25                  30

Ile Ala Lys
        35

<210> SEQ ID NO 34
<211> LENGTH: 45
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 34

Met Lys Lys Asn Gln Phe Leu Lys Glu Ser Asp Val Thr Ala Glu Ser
 1               5                  10                  15

Val Phe Phe Met Lys Arg Arg Gln Val Leu Lys Ala Leu Gly Ile Ser
                20                  25                  30

Ala Thr Ala Leu Ser Leu Pro His Ala Ala His Ala Asp
        35                  40                  45

<210> SEQ ID NO 35
<211> LENGTH: 31
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 35

Met Ser Gly Leu Pro Leu Ile Ser Arg Arg Arg Leu Leu Thr Ala Met
 1               5                  10                  15

Ala Leu Ser Pro Leu Leu Trp Gln Met Asn Thr Ala His Ala Ala
                20                  25                  30

<210> SEQ ID NO 36
<211> LENGTH: 28
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 36

Met Asn Arg Arg Asn Phe Ile Lys Ala Ala Ser Cys Gly Ala Leu Leu
 1               5                  10                  15

Thr Gly Ala Leu Pro Ser Val Ser His Ala Ala Ala
                20                  25
```

```
<210> SEQ ID NO 37
<211> LENGTH: 33
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 37

Met Asp Arg Arg Arg Phe Ile Lys Gly Ser Met Ala Met Ala Ala Val
 1               5                  10                  15

Cys Gly Thr Ser Gly Ile Ala Ser Leu Phe Ser Gln Ala Ala Phe Ala
            20                  25                  30

Ala

<210> SEQ ID NO 38
<211> LENGTH: 28
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 38

Met Ser Leu Ser Arg Arg Gln Phe Ile Gln Ala Ser Gly Ile Ala Leu
 1               5                  10                  15

Cys Ala Gly Ala Val Pro Leu Lys Ala Ser Ala Ala
            20                  25

<210> SEQ ID NO 39
<211> LENGTH: 49
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 39

Met Ser Asn Gln Gly Glu Tyr Pro Glu Asp Asn Arg Val Gly Lys His
 1               5                  10                  15

Glu Pro His Asp Leu Ser Leu Thr Arg Arg Asp Leu Ile Lys Val Ser
            20                  25                  30

Ala Ala Thr Ala Ala Thr Ala Val Val Tyr Pro His Ser Thr Leu Ala
        35                  40                  45

Ala

<210> SEQ ID NO 40
<211> LENGTH: 45
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 40

Met Ser Trp Ile Gly Trp Thr Val Ala Ala Thr Ala Leu Gly Asp Asn
 1               5                  10                  15

Gln Met Ser Phe Thr Arg Arg Lys Phe Val Leu Gly Met Gly Thr Val
            20                  25                  30

Ile Phe Phe Thr Gly Ser Ala Ser Ser Leu Leu Ala Asn
        35                  40                  45
```

```
<210> SEQ ID NO 41
<211> LENGTH: 38
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 41

Met Thr Gly Asp Asn Thr Leu Ile His Ser His Gly Ile Asn Arg Arg
 1               5                  10                  15

Asp Phe Met Lys Leu Cys Ala Ala Leu Ala Ala Thr Met Gly Leu Ser
                20                  25                  30

Ser Lys Ala Ala Ala Glu
            35

<210> SEQ ID NO 42
<211> LENGTH: 47
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 42

Met Met Lys Ile His Thr Thr Glu Ala Leu Met Lys Ala Glu Ile Ser
 1               5                  10                  15

Arg Arg Ser Leu Met Lys Thr Ser Ala Leu Gly Ser Leu Ala Leu Ala
                20                  25                  30

Ser Ser Ala Phe Thr Leu Pro Phe Ser Gln Met Val Arg Ala Ala
            35                  40                  45

<210> SEQ ID NO 43
<211> LENGTH: 46
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 43

Met Lys Thr Lys Ile Pro Asp Ala Val Leu Ala Ala Glu Val Ser Arg
 1               5                  10                  15

Arg Gly Leu Val Lys Thr Thr Ala Ile Gly Gly Leu Ala Met Ala Ser
                20                  25                  30

Ser Ala Leu Thr Leu Pro Phe Ser Arg Ile Ala His Ala Val
            35                  40                  45

<210> SEQ ID NO 44
<211> LENGTH: 44
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 44

Met Ser Lys Asn Glu Arg Met Val Gly Ile Ser Arg Arg Thr Leu Val
 1               5                  10                  15

Lys Ser Thr Ala Ile Gly Ser Leu Ala Leu Ala Ala Gly Gly Phe Ser
                20                  25                  30

Leu Pro Phe Thr Leu Arg Asn Ala Ala Ala Ala Val
            35                  40
```

```
<210> SEQ ID NO 45
<211> LENGTH: 34
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 45

Met Gln Val Ser Arg Arg Gln Phe Phe Lys Ile Cys Ala Gly Gly Met
1               5                   10                  15

Ala Gly Thr Thr Ala Ala Ala Leu Gly Phe Ala Pro Ser Val Ala Leu
            20                  25                  30

Ala Glu

<210> SEQ ID NO 46
<211> LENGTH: 62
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 46

Met Thr Asp Tyr Ala Ser Phe Ala Lys Val Ser Gly Gln Ile Ser Arg
1               5                   10                  15

Leu Leu Val Thr Gln Leu Arg Phe Leu Leu Leu Gly Arg Gly Met Ser
            20                  25                  30

Gly Ser Asn Thr Ala Ile Ser Arg Arg Arg Leu Leu Gln Gly Ala Gly
        35                  40                  45

Ala Met Trp Leu Leu Ser Val Ser Gln Val Ser Leu Ala Ala
        50                  55                  60

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 47

Arg Arg Arg Gly Phe Leu Thr
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 48

Gln Arg Arg Arg Ala Leu Thr
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide
```

```
<400> SEQUENCE: 49

Thr Arg Arg Glu Phe Ile Lys
  1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 50

Ser Arg Arg Ser Phe Met Lys
  1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 51

Gly Arg Arg Arg Phe Leu Arg
  1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 52

Ser Arg Arg Gln Phe Phe Lys
  1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 53

Ser Arg Arg Arg Phe Leu Gln
  1               5

<210> SEQ ID NO 54
<211> LENGTH: 54
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 54
gcgatggagc tcttaaagag gagaaaggtc atgccattta aaaaactctc ccga          54

<210> SEQ ID NO 55
<211> LENGTH: 48
<212> TYPE: DNA
<213> ORGANISM: Artificial Sequence
```

-continued

```
<220> FEATURE:
<223> OTHER INFORMATION: Description of Artificial Sequence: Synthetic
      Primer

<400> SEQUENCE: 55
gcgatggagc tcttaaagag gagaaaggtc atgacctggt ctcgtcgc                    48

<210> SEQ ID NO 56
<211> LENGTH: 48
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 56
gcgatggagc tcttaaagag gagaaaggtc atgaaagaaa gcaatagc                    48

<210> SEQ ID NO 57
<211> LENGTH: 57
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 57
gcgatggagc tcttaaagag gagaaaggtc atgaataacg aggaaacatt ttaccag         57

<210> SEQ ID NO 58
<211> LENGTH: 48
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 58
gcgatggagc tcttaaagag gagaaaggtc gtggggagac gacgcgga                    48

<210> SEQ ID NO 59
<211> LENGTH: 48
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 59
gcgatggagc tcttaaagag gagaaaggtc atgcaacgtc gtgatttc                    48

<210> SEQ ID NO 60
<211> LENGTH: 48
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 60
gcgatggagc tcttaaagag gagaaaggtc atgtcccggt cagcgaaa                    48

<210> SEQ ID NO 61
<211> LENGTH: 48
<212> TYPE: DNA
<213> ORGANISM: Artificial Sequence
<220> FEATURE:
```

<223> OTHER INFORMATION: Description of Artificial Sequence: Synthetic
     Primer

<400> SEQUENCE: 61
gcgatggagc tcttaaagag gagaaaggtc atggacaaat tcgacgct                48

<210> SEQ ID NO 62
<211> LENGTH: 48
<212> TYPE: DNA
<213> ORGANISM: Artificial Sequence
<220> FEATURE:
<223> OTHER INFORMATION: Description of Artificial Sequence: Synthetic
     Primer

<400> SEQUENCE: 62
gcgatggagc tcttaaagag gagaaaggtc atgcgacaca tttttcaa                48

<210> SEQ ID NO 63
<211> LENGTH: 53
<212> TYPE: DNA
<213> ORGANISM: Artificial Sequence
<220> FEATURE:
<223> OTHER INFORMATION: Description of Artificial Sequence: Synthetic
     Primer

<400> SEQUENCE: 63
gcgatggagc tcttaaagag gagaaaggtc atgcagtata aagatgaaaa cgg          53

<210> SEQ ID NO 64
<211> LENGTH: 48
<212> TYPE: DNA
<213> ORGANISM: Artificial Sequence
<220> FEATURE:
<223> OTHER INFORMATION: Description of Artificial Sequence: Synthetic
     Primer

<400> SEQUENCE: 64
gcgatggagc tcttaaagag gagaaaggtc atgagcactt ttaaacca                48

<210> SEQ ID NO 65
<211> LENGTH: 59
<212> TYPE: DNA
<213> ORGANISM: Artificial Sequence
<220> FEATURE:
<223> OTHER INFORMATION: Description of Artificial Sequence: Synthetic
     Primer

<400> SEQUENCE: 65
gcgatggagc tcttaaagag gagaaaggtc atgaaaaaga atcaatttt aaaagaatc     59

<210> SEQ ID NO 66
<211> LENGTH: 48
<212> TYPE: DNA
<213> ORGANISM: Artificial Sequence
<220> FEATURE:
<223> OTHER INFORMATION: Description of Artificial Sequence: Synthetic
     Primer

<400> SEQUENCE: 66
gcgatggagc tcttaaagag gagaaaggtc atgagcggct tacctctt                48

<210> SEQ ID NO 67
<211> LENGTH: 48
<212> TYPE: DNA
<213> ORGANISM: Artificial Sequence
<220> FEATURE:
<223> OTHER INFORMATION: Description of Artificial Sequence: Synthetic -continued Primer

<400> SEQUENCE: 67
gcgatggagc tcttaaagag gagaaaggtc atgattcggc aacgtcgt        48

<210> SEQ ID NO 68
<211> LENGTH: 48
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 68
gcgatggagc tcttaaagag gagaaaggtc atgatcaggg aggaagtt        48

<210> SEQ ID NO 69
<211> LENGTH: 62
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 69
gcgatggagc tcttaaagag gagaaaggtc gtgaacagac gtaattttat taaagcagcc    60
tc                                                                  62

<210> SEQ ID NO 70
<211> LENGTH: 48
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 70
gcgatggagc tcttaaagag gagaaaggtc atggatcgta gacgattt        48

<210> SEQ ID NO 71
<211> LENGTH: 48
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 71
gcgatggagc tcttaaagag gagaaaggtc atgtcactca gtcggcgt        48

<210> SEQ ID NO 72
<211> LENGTH: 48
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 72
gcgatggagc tcttaaagag gagaaaggtc atgagcaacc aaggcgaa        48

<210> SEQ ID NO 73
<211> LENGTH: 48
<212> TYPE: DNA
<213> ORGANISM: Artificial Sequence
<220> FEATURE:

-continued

<223> OTHER INFORMATION: Description of Artificial Sequence: Synthetic
     Primer

<400> SEQUENCE: 73
gcgatggagc tcttaaagag gagaaaggtc atgtcatgga tagggtgg                48

<210> SEQ ID NO 74
<211> LENGTH: 48
<212> TYPE: DNA
<213> ORGANISM: Artificial Sequence
<220> FEATURE:
<223> OTHER INFORMATION: Description of Artificial Sequence: Synthetic
     Primer

<400> SEQUENCE: 74
gcgatggagc tcttaaagag gagaaaggtc atgactggag ataacacc                48

<210> SEQ ID NO 75
<211> LENGTH: 48
<212> TYPE: DNA
<213> ORGANISM: Artificial Sequence
<220> FEATURE:
<223> OTHER INFORMATION: Description of Artificial Sequence: Synthetic
     Primer

<400> SEQUENCE: 75
gcgatggagc tcttaaagag gagaaaggtc atgaaactca gtcgtcgt                48

<210> SEQ ID NO 76
<211> LENGTH: 57
<212> TYPE: DNA
<213> ORGANISM: Artificial Sequence
<220> FEATURE:
<223> OTHER INFORMATION: Description of Artificial Sequence: Synthetic
     Primer

<400> SEQUENCE: 76
gcgatggagc tcttaaagag gagaaaggtc atgatgaaaa tccataccac agaggcg      57

<210> SEQ ID NO 77
<211> LENGTH: 52
<212> TYPE: DNA
<213> ORGANISM: Artificial Sequence
<220> FEATURE:
<223> OTHER INFORMATION: Description of Artificial Sequence: Synthetic
     Primer

<400> SEQUENCE: 77
gcgatggagc tcttaaagag gagaaaggtc atgaaaacga aaatccctga tg           52

<210> SEQ ID NO 78
<211> LENGTH: 54
<212> TYPE: DNA
<213> ORGANISM: Artificial Sequence
<220> FEATURE:
<223> OTHER INFORMATION: Description of Artificial Sequence: Synthetic
     Primer

<400> SEQUENCE: 78
gcgatggagc tcttaaagag gagaaaggtc atgtccaaaa atgaacgaat ggtg         54

<210> SEQ ID NO 79
<211> LENGTH: 48
<212> TYPE: DNA
<213> ORGANISM: Artificial Sequence
<220> FEATURE:
<223> OTHER INFORMATION: Description of Artificial Sequence: Synthetic -continued

```
      Primer

<400> SEQUENCE: 79
gcgatggagc tcttaaagag gagaaaggtc atggacgtca gtcgcaga                48

<210> SEQ ID NO 80
<211> LENGTH: 48
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 80
gcgatggagc tcttaaagag gagaaaggtc atgcaggtca gcagaagg                48

<210> SEQ ID NO 81
<211> LENGTH: 60
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 81
gcgatggagc tcttaaagag gagaaaggtc atgacagatt atgcgtcttt cgctaaagtt   60

<210> SEQ ID NO 82
<211> LENGTH: 48
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 82
gcgatggagc tcttaaagag gagaaaggtc atgatttcac gccgccga                48

<210> SEQ ID NO 83
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 83
gcgatgtcta gagctttgtc gggcgggaag                                    30

<210> SEQ ID NO 84
<211> LENGTH: 36
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 84
gcgatgtcta gaattgatat tcaacgtttt cgccac                             36

<210> SEQ ID NO 85
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer
```

```
<400> SEQUENCE: 85
gcgatgtcta gatagggtgc cagctaccgc                                        30

<210> SEQ ID NO 86
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 86
gcgatgtcta gagcgcggtt tgttctccag                                        30

<210> SEQ ID NO 87
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 87
gcgatgtcta gatacgcgcc cgatatggtt                                        30

<210> SEQ ID NO 88
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 88
gcgatgtcta gataacgttg ggcgttctgc                                        30

<210> SEQ ID NO 89
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 89
gcgatgtcta gagcgcaacc gcacgccaga                                        30

<210> SEQ ID NO 90
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 90
gcgatgtcta gagcgtgggg tagagagtgt                                        30

<210> SEQ ID NO 91
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer
```

```
<400> SEQUENCE: 91
gcgatgtcta gacgtatcaa tggctggctt                                              30

<210> SEQ ID NO 92
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 92
gcgatgtcta gacgcacttt gcgttttttg                                              30

<210> SEQ ID NO 93
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 93
gcgatgtcta gattttaaaa gttcgtcttt gg                                           32

<210> SEQ ID NO 94
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 94
gcgatgtcta gaaaaccagc taagcagatc                                              30

<210> SEQ ID NO 95
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 95
gcgatgtcta gaattgggat caatagccgc                                              30

<210> SEQ ID NO 96
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 96
gcgatgtcta gagaatacag cgaccgtatg                                              30

<210> SEQ ID NO 97
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 97
```
gcgatgtcta gatttaccgc ccttctcttc          30

<210> SEQ ID NO 98
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 98
gcgatgtcta gatggcgggc ggttttcagc          30

<210> SEQ ID NO 99
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 99
gcgatgtcta gaggcaatat cagaatctgc          30

<210> SEQ ID NO 100
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 100
gcgatgtcta gacggttgct gttgcccggc          30

<210> SEQ ID NO 101
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 101
gcgatgtcta gaagctgccg gaacgcttgc          30

<210> SEQ ID NO 102
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 102
gcgatgtcta gactttctt gcctcgtgtt          30

<210> SEQ ID NO 103
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 103

-continued gcgatgtcta gaaaccgatt cggccatctc         30

<210> SEQ ID NO 104
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 104
gcgatgtcta gactgaccaa caacggcgcg         30

<210> SEQ ID NO 105
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 105
gcgatgtcta gattctaccg gagcctctgc         30

<210> SEQ ID NO 106
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 106
gcgatgtcta gatggaatgg cgctatcgac         30

<210> SEQ ID NO 107
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 107
gcgatgtcta gattttcgc gggcctgttg         30

<210> SEQ ID NO 108
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 108
gcgatgtcta gataatttgt agtttcgcgc ctg         33

<210> SEQ ID NO 109
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 109
gcgatgtcta gacagtttat actgccgggt ttc         33

<210> SEQ ID NO 110
<211> LENGTH: 30
<212> TYPE: DNA
<213> ORGANISM: Artificial Sequence
<220> FEATURE:
<223> OTHER INFORMATION: Description of Artificial Sequence: Synthetic Primer

<400> SEQUENCE: 110
gcgatgtcta gacgccacga cctggctgac                               30

<210> SEQ ID NO 111
<211> LENGTH: 30
<212> TYPE: DNA
<213> ORGANISM: Artificial Sequence
<220> FEATURE:
<223> OTHER INFORMATION: Description of Artificial Sequence: Synthetic Primer

<400> SEQUENCE: 111
gcgatgtcta gagctcgtgg ctatcgtcgc                               30

<210> SEQ ID NO 112
<211> LENGTH: 36
<212> TYPE: DNA
<213> ORGANISM: Artificial Sequence
<220> FEATURE:
<223> OTHER INFORMATION: Description of Artificial Sequence: Synthetic Primer

<400> SEQUENCE: 112
gcgatgtcta gaagtaaagg agaagaactt ttcact                        36

<210> SEQ ID NO 113
<211> LENGTH: 33
<212> TYPE: DNA
<213> ORGANISM: Artificial Sequence
<220> FEATURE:
<223> OTHER INFORMATION: Description of Artificial Sequence: Synthetic Primer

<400> SEQUENCE: 113
gcgatgaagc ttctatttgt atagttcatc cat                           33

<210> SEQ ID NO 114
<211> LENGTH: 81
<212> TYPE: DNA
<213> ORGANISM: Artificial Sequence
<220> FEATURE:
<223> OTHER INFORMATION: Description of Artificial Sequence: Synthetic Primer

<400> SEQUENCE: 114
gcgatgaagc ttgcatgctt aagctgctaa agcgtagttt tcgtcgtttg ctgcgtcgac    60
tttgtatagt tcatccatgc c                                        81

<210> SEQ ID NO 115
<211> LENGTH: 60
<212> TYPE: DNA
<213> ORGANISM: Artificial Sequence
<220> FEATURE:
<223> OTHER INFORMATION: Description of Artificial Sequence: Synthetic Primer

<400> SEQUENCE: 115

-continued gcgatggaat tcgagctctt aaagaggaga aaggtcatga acaataacga tctctttcag    60

<210> SEQ ID NO 116
<211> LENGTH: 36
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 116
gcgatgtcta gaagcgtcag tcgccgcttg cgccgc    36

<210> SEQ ID NO 117
<211> LENGTH: 60
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 117
gcgatggaat tcgagctctt aaagaggaga aaggtcgtga acaaagcac tattgcactg    60

<210> SEQ ID NO 118
<211> LENGTH: 35
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 118
gcgatgaagc ttttatttca gccccagagc ggctt    35

<210> SEQ ID NO 119
<211> LENGTH: 11
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 119

Ala Ala Asn Asp Glu Asn Tyr Ala Leu Ala Ala
 1               5                  10

<210> SEQ ID NO 120
<211> LENGTH: 45
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 120

Met Asn Asn Asn Asp Leu Phe Gln Ala Ser Arg Arg Arg Phe Leu Ala
 1               5                  10                  15

Gln Leu Gly Gly Leu Thr Val Ala Gly Met Leu Gly Pro Ser Leu Leu
            20                  25                  30

Thr Pro Arg Arg Ala Thr Ala Ala Gln Ala Ala Thr Asp
        35                  40                  45

<210> SEQ ID NO 121
<211> LENGTH: 46
<212> TYPE: PRT

<213> ORGANISM: Artificial Sequence
<220> FEATURE:
<223> OTHER INFORMATION: Description of Artificial Sequence: Synthetic
      Peptide

<400> SEQUENCE: 121

Met Asn Asn Asn Asp Leu Phe Gln Thr Ser Arg Arg Arg Leu Leu Ala
1               5                   10                  15

Gln Leu Gly Gly Leu Thr Val Ala Gly Met Leu Gly Pro Ser Leu Leu
            20                  25                  30

Thr Pro Arg Arg Ala Thr Ala Ala Gln Ala Ala Thr Asp Ala
        35                  40                  45

<210> SEQ ID NO 122
<211> LENGTH: 46
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 122

Met Asn Asn Asn Asp Leu Phe Gln Thr Ser Arg Gln Arg Phe Leu Ala
1               5                   10                  15

Gln Leu Gly Gly Leu Thr Val Ala Gly Met Leu Gly Pro Ser Leu Leu
            20                  25                  30

Thr Pro Arg Arg Ala Thr Ala Ala Gln Ala Ala Thr Asp Ala
        35                  40                  45

<210> SEQ ID NO 123
<211> LENGTH: 46
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 123

Met Asn Asn Asn Asp Ile Phe Gln Ala Ser Arg Arg Arg Phe Leu Ala
1               5                   10                  15

Gln Pro Gly Gly Leu Thr Val Ala Gly Met Leu Gly Pro Ser Leu Leu
            20                  25                  30

Thr Pro Arg Arg Ala Thr Ala Ala Gln Ala Ala Thr Asp Ala
        35                  40                  45

<210> SEQ ID NO 124
<211> LENGTH: 46
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 124

Met Asn Asn Asn Glu Leu Phe Gln Ala Ser Arg Arg Arg Phe Leu Ala
1               5                   10                  15

Gln Leu Gly Gly Leu Thr Val Ala Gly Met Leu Gly Pro Ser Leu Leu
            20                  25                  30

Thr Pro Arg Arg Ala Thr Ala Ala Gln Ala Ala Thr Asp Ala
        35                  40                  45

<210> SEQ ID NO 125
<211> LENGTH: 46

```
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 125

Met Asn Asn Asn Asp Leu Phe Gln Thr Thr Arg Arg Arg Phe Leu Ala
 1               5                  10                  15

Gln Leu Gly Gly Leu Thr Val Ala Gly Met Leu Gly Pro Ser Leu Leu
            20                  25                  30

Thr Pro Arg Arg Ala Thr Ala Ala Gln Ala Ala Thr Asp Ala
        35                  40                  45

<210> SEQ ID NO 126
<211> LENGTH: 46
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 126

Met Asn Asn Asn Asp Ser Phe Gln Thr Ser Arg Arg Arg Phe Leu Ala
 1               5                  10                  15

Gln Leu Gly Gly Leu Thr Val Ala Gly Met Leu Gly Pro Ser Leu Leu
            20                  25                  30

Thr Pro Arg Arg Ala Thr Ala Ala Gln Ala Ala Thr Asp Ala
        35                  40                  45

<210> SEQ ID NO 127
<211> LENGTH: 35
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 127

Met Ser Thr Phe Lys Pro Leu Lys Thr Leu Thr Ser Arg Arg Gln Val
 1               5                  10                  15

Leu Lys Ala Gly Leu Ala Ala Leu Thr Leu Ser Gly Met Ser Gln Ala
            20                  25                  30

Ile Ala Lys
        35

<210> SEQ ID NO 128
<211> LENGTH: 46
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 128

Met Lys Thr Lys Ile Pro Asp Ala Val Leu Ala Ala Glu Val Ser Arg
 1               5                  10                  15

Arg Gly Leu Val Lys Thr Thr Ala Ile Gly Gly Leu Ala Met Ala Ser
            20                  25                  30

Ser Ala Leu Thr Leu Pro Phe Ser Arg Ile Ala His Ala Val
        35                  40                  45

<210> SEQ ID NO 129
```

```
<211> LENGTH: 84
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 129
gcgatggagc tcttaaagag gagaaaggtc atgaacaata acgatctctt tcaggcatca      60
aagaaacgtt ttctggcaca actc                                            84

<210> SEQ ID NO 130
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 130
gcgatgtcta gacggacacc agaaatgcct gt                                   32

<210> SEQ ID NO 131
<211> LENGTH: 35
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 131
gcgatgaagc ttttatttca gccccagagc ggctt                                35

<210> SEQ ID NO 132
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 132
gctgctagcg aagttcaact gcaacag                                         27

<210> SEQ ID NO 133
<211> LENGTH: 36
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 133
gcgatgcccg ggggctttgt tagcagccgg atctca                               36

<210> SEQ ID NO 134
<211> LENGTH: 45
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 134
gcgctgttgc agttgaactt cgctagcagc gtcagtcgcc gcttg                     45
```

ENGINEERING OF LEADER PEPTIDES FOR THE SECRETION OF RECOMBINANT PROTEINS IN BACTERIA

This application claims the priority of U.S. Provisional Patent Application Ser. No. 60/337,452, filed Nov. 5, 2001, and U.S. Provisional Patent Application Ser. No. 60/404,944, filed Aug. 21, 2002, in the name of George Georgiou and Matthew DeLisa and entitled "Engineering of Leader Peptides for the Secretion of Recombinant Proteins in Bacteria." Both of the foregoing disclosures are specifically incorporated herein by reference in the entirety.

BACKGROUND OF THE INVENTION

1. Field of the Invention

The present invention relates generally to the fields of genetic engineering and protein secretion. More specifically, the present invention relates to engineering of leader peptides for the secretion of recombinant proteins in bacteria.

2. Description of the Related Art

Proteins destined for secretion from the cytoplasm are synthesized with an N-terminal peptide extension of generally between 15–30 amino acids known as the leader peptide. The leader peptide is proteolytically removed from the mature protein either concomitant to or immediately following export into an exocytoplasmic location.

Recent findings have established that there are actually four protein export pathways in Gram-negative bacteria (Stuart and Neupert, 2000): the general secretory (Sec) pathway (Danese and Silhavy, 1998; Pugsley, 1993), the signal recognition particle (SRP)-dependent pathway (Meyer et al., 1982), the recently discovered YidC-dependent pathway (Samuelson et al., 2000) and the twin-arginine translocation (Tat) system (Berks, 1996). With the first three of these pathways, polypeptides cross the membrane via a 'threading' mechanism, i.e., the unfolded polypeptides insert into a pore-like structure formed by the proteins SecY, SecE and SecG and are pulled across the membrane via a process that requires the hydrolysis of ATP (Schatz and Dobberstein, 1996).

In contrast, proteins exported through the Tat-pathway transverse the membrane in a partially or perhaps even fully folded conformation. The bacterial Tat system is closely related to the 'ΔpH-dependent' protein import pathway of the plant chloroplast thylakoid membrane (Settles et al., 1997). Export through the Tat pathway does not require ATP hydrolysis and does not involve passage through the SecY/E/G pore. In most instances, the natural substrates for this pathway are proteins that have to fold in the cytoplasm in order to acquire a range of cofactors such as FeS centers or molybdopterin. However, proteins that do not contain cofactors but fold too rapidly or too tightly to be exported via any other pathway can be secreted from the cytoplasm by fusing them to a Tat-specific leader peptide (Berks, 1996; Berks et al., 2000).

The membrane proteins TatA, TatB and TatC are essential components of the Tat translocase in E. coli Sargent et al., 1998; Weiner et al., 1998). In addition, the TatA homologue TatE, although not essential, may also has a role in translocation and the involvement of other factors cannot be ruled out. TatA, TatB and TatE are all integral membrane proteins predicted to span the inner membrane once with their C-terminal domain facing the cytoplasm. The TatA and B proteins are predicted to be single-span proteins, whereas the TatC protein has six transmembrane segments and has been proposed to function as the translocation channel and receptor for preproteins (Berks et al., 2000; Bogsch et al., 1998; Chanal et al., 1998). Mutagenesis of either TatB or C completely abolishes export (Bogsch et al., 1998; Sargent et al., 1998; Weiner et al., 1998). The Tat complex purified from solubilized E. coli membranes contained only TatABC (Bolhuis et al., 2001). In vitro reconstitution of the translocation complex demonstrated a minimal requirement for TatABC and an intact membrane potential (Yahr and Wickner, 2001).

The choice of the leader peptides, and thus the pathway employed in the export of a particular protein, can determine whether correctly folded functional protein will be produced (Bowden and Georgiou, 1990; Thomas et al., 2001). Feilmeier et al. (2000) have shown that fusion of the green fluorescent protein (GFP) to a Sec-specific leader peptide or to the C-terminal of the maltose binding protein (MBP which is also exported via the Sec pathway) resulted in export of green fluorescent protein and MBP-GFP into the periplasm. However, green fluorescent protein in the periplasm was non-fluorescent indicating that the secreted protein was misfolded and thus the chromophore of the green fluorescent protein could not be formed. Since proteins exported via the Sec pathway transverse the membrane in an unfolded form, it was concluded that the environment in the bacterial secretory compartment (the periplasmic space) does not favor the folding of green fluorescent protein Feilmeier et al., 2000). In contrast, fusion of a Tat-specific leader peptide to green fluorescent protein resulted in accumulation of fluorescent green fluorescent protein in the periplasmic space. In this case, the Tat-GFP propeptide was first able to fold in the cytoplasm and then be exported into the periplasmic space as a completely folded protein (Santini et al., 2001; Thomas et al., 2001). However, there has been no evidence that leader peptides other than TorA can be employed to export heterologous proteins into the periplasmic space of E. coli.

The cellular compartment where protein folding takes place can have a dramatic effect on the yield of biological active protein. The bacterial cytoplasm contains a large number of protein folding accessory factors, such as chaperones whose function and ability to facilitate folding of newly synthesized polypeptides is controlled by ATP hydrolysis. In contrast, the bacterial periplasm contains relatively few chaperones and there is no evidence that ATP is present in that compartment. Thus many proteins are unable to fold in the periplasm and can reach their native state only within the cytoplasmic milieu. The only known way to enable the secretion of folded proteins from the cytoplasm is via fusion to a Tat-specific leader peptide. However, the protein flux through the Tat export system is significantly lower than that of the more widely used Sec pathway. Consequently, the accumulation and steady state yield of proteins exported via the Tat pathway is low.

The prior art is thus deficient in methods of directing efficient export of folded proteins from the cytoplasm. The present invention fulfills this long-standing need and desire in the art.

SUMMARY OF THE INVENTION

The present invention provides methods for the isolation of sequences that can serve as leader peptides to direct the export of heterologous proteins. One aspect of the invention allows the isolation of leader peptides capable of directing proteins to the Tat secretion pathway. Further, the present invention discloses methods for identifying leader peptide mutants that can confer improved protein export.

In one aspect, the invention thus provides methods of identifying leader peptides that direct enhanced protein secretion in bacteria. In one embodiment, the methods disclosed herein comprise screening libraries of mutated leader peptides for sequences that allow rapid export and thus can rescue a short-lived reporter protein from degradation in the cytoplasm. Leader peptides that mediate secretion through the *Escherichia coli* Twin Arginine Translocation (Tat) pathway, as well as those that direct other secretion pathways such as the sec pathway in bacteria can be isolated by the methods disclosed herein. Mutant leader peptide sequences conferring improved export are also disclosed. The mutant leader peptides are shown to confer significantly higher steady state levels of export not only for the short lived reporter protein but also for other stable, long lived proteins.

In one aspect of the present invention, there is provided a method of identifying leader peptides that direct increased protein export through pathways that include, but are not limited to, the Twin Arginine Translocation (TAT) pathway and the sec pathway. Such a method may involve constructing expression cassettes that place mutated leader peptides upstream of a gene encoding a short-lived reporter protein. The short-lived reporter protein can be created by attaching a cytoplasmic degradation sequence to the gene encoding the reporter protein. The resulting expression cassettes may then be expressed in bacteria, and reporter protein expressions in these bacteria measured. Mutated leader peptides expressed in cells that exhibit increased reporter protein expression comprise leader peptides that would direct increased protein export in bacteria. Representative leader peptides identified from the above methods include SEQ ID NOs:120–136.

In another aspect of the present invention, there is provided a method of increasing polypeptide export through pathways that include, but are not limited to, the Tat pathway and the sec pathway. This method involves expressing expression cassettes that place mutated leader peptides identified in the methods disclosed herein upstream of the gene encoding a heterologous polypeptide of interest.

In yet another aspect of the present invention, there is provided a method of screening for a compound that inhibits or enhances protein export through pathways that include, but are not limited to, the Tat pathway and the sec pathway. This method may comprise first constructing expression cassettes that place mutated leader peptides identified in the methods disclosed herein upstream of a gene encoding a short-lived reporter protein. The short-lived reporter protein can be created by attaching a cytoplasmic degradation sequence to the gene encoding the reporter protein. The resulting expression cassettes may then be expressed in bacteria, and reporter protein expression in these bacteria are measured in the presence or absence of the candidate compound. Increased reporter protein expression measured in the presence of the candidate compound indicates that the candidate compound enhances protein export, whereas decreased reporter protein expression measured in the presence of the candidate compound indicates that the candidate compound inhibits protein export.

In another aspect of the present invention, there is provided a method for producing soluble and biologically-active heterologous polypeptide containing multiple disulfide bonds in a bacterial cell. The method may involve constructing an expression cassette that places a leader peptide that directs protein export through the Twin Arginine Translocation pathway upstream of a gene encoding the heterologous polypeptide. The heterologous polypeptide is then expressed in bacteria that have an oxidizing cytoplasm.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention as well as others which will become clear are attained and can be understood in detail, more particular descriptions and certain embodiments of the invention briefly summarized above are illustrated in the appended drawings. These drawings form a part of the specification. The drawings illustrate certain embodiments of the invention and are not to be considered limiting in their scope.

FIG. 1A shows minimal green fluorescent protein fluorescence in cells expressing pGFPSsrA, indicating that cytoplasmic SsrA-tagged green fluorescent protein is degraded almost completely. FIG. 1B shows enhanced green fluorescent protein fluorescence in cells expressing pTorAGFPSsrA, indicating improved green fluorescent protein export directed by the TorA leader peptide. FIG. 1C shows green fluorescent protein fluorescence in cells expressing pTorAGFP. The green fluorescent protein was expressed in both the cytoplasm and the periplasm.

FIG. 3A shows western blot of green fluorescent protein in the periplasm (lanes 1–3) and cytoplasm (lanes 4–6) of cells expressing the wild type construct (lanes 1 and 4), the B6 clone (lanes 2 and 5) and the E2 clone (lanes 3 and 6). GroEL is a cytoplasmic marker whereas DsbA is a periplasmic marker. FIG. 3B shows periplasmic and cytoplasmic distribution of green fluorescent protein in cells expressing the wild type construct, the B6 clone and the E2 clone.

DETAILED DESCRIPTION OF THE INVENTION

Figure 1:
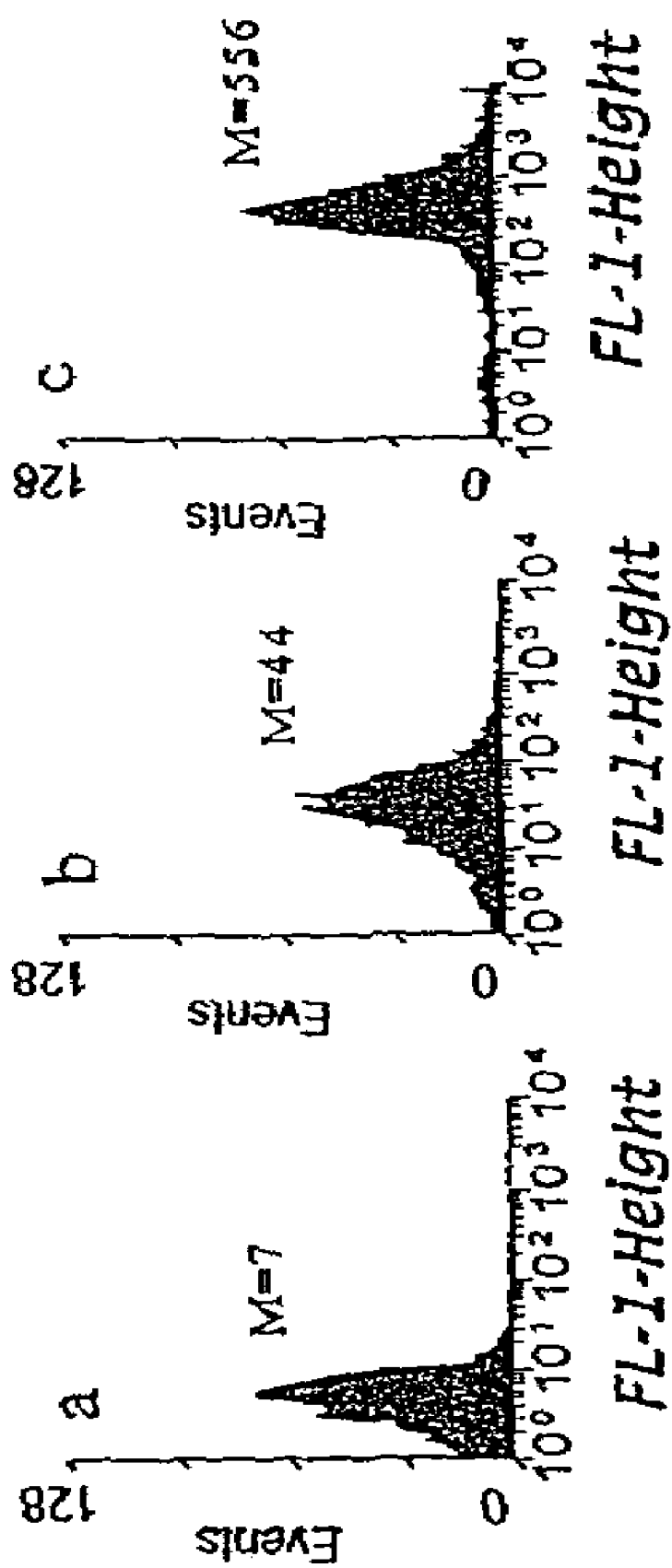
FIG. 1 shows the expression of green fluorescent protein in different plasmid constructs.

The present invention provides methods of identifying and using leader peptides that direct enhanced protein secretion in bacteria. Numerous proteins of commercial interest are produced in secreted form in bacteria. However, many proteins, including many antibody fragments and several enzymes of eucaryotic origin, cannot be exported efficiently through the main secretory pathway, the sec pathway, of bacteria.

An alternative pathway for the translocation of proteins from the cytoplasm of bacteria is called the "TAT" (twin-arginine-translocation) pathway. Whether a protein is directed to the sec machinery or the TAT pathway depends solely on the nature of the leader peptide, an amino acid extension of generally 15–30 residues located at the beginning of the polypeptide chain. The leader peptide consists of three distinct regions: (1) the amino terminal n-region, (2) the hydrophobic core or h-region, and (3) the c-terminal region.

A hallmark of both plant and prokaryotic TAT-specific leader peptides is the presence of the distinctive and conserved (S/T)-R-R-x-F-L-K (SEQ ID NO:1) sequence motif. This sequence motif is located at the n-region/h-boundary within leader peptides of known and predicted TAT substrates (Berks, 1996). Mutation of either arginine residue within the signal peptide significantly reduces the efficiency of protein translocation (Cristobal et al., 1999).

Relative to leader peptides specific for the Sec pathway, which is by far the most commonly used export pathway in bacteria, TAT-specific leader peptides are on average 14 amino acids longer due to an extended n-region and more basic residues in the c-region (Cristobal et al., 1999). However, the hydrophobic h-region in the TAT-specific leader peptides is significantly shorter due to a higher occurrence of glycine and threonine residues.

The twin-arginine (RR) motifs of wheat pre-23K and pre-Hcf136 are essential for targeting by the thylakoid TAT pathway; this motif is probably a central feature of TAT signals. The twin-arginine motif is not the only important determinant in TAT-specific targeting signals, and a further hydrophobic residue two or three residues after this motif seems also to be highly important.

Bacterial twin-arginine-signal peptides are similar to thylakoid TAT signals and can direct TAT-dependent targeting into plant thylakoids with high efficiency. However, the vast majority of bacterial signal peptides contain conserved sequence elements in addition to the twin-arginine motif that imply special functions. There is a heavy bias towards phenylalanine at the second position after the twin-arginine motif, and many of the signals contain lysine at the fourth position. None of the known thylakoid twin-arginine signals contains phenylalanine at this position and only one (Arabidopsis P29) contains lysine as the fourth residue after the twin-arginine motif. The precise roles of these highly conserved features are unclear; the phenylalanine residue can be replaced by Leu but not by Ala without undue effects, which indicates that hydrophobicity, rather than the phenylalanine side-chain, might be the important determinant. Similarly, replacement of the Lys residue does not impede export (Robinson and Bolhuis, 2001).

Proteins exported through the TAT system first fold into their native conformation within the cytoplasm and are then exported across the cytoplasmic membrane. The ability to export proteins that have already folded in the cytoplasm is highly desirable with regard to commercial protein production for several reasons. First of all, proteins that fold very rapidly after synthesis is completed cannot be secreted by the more common sec export pathway. Secondly, the bacterial cytoplasm contains a full complement of folding accessory factors, which can assist a nascent polypeptide in reaching its native conformation. In contrast, the secretory compartment of bacteria contains very few folding accessory factors such as chaperones and foldases. Therefore, for the production of many proteins, it is preferable for folding to occur first within the cytoplasm followed by export into the periplasmic space through the TAT system. Thirdly, the acquisition of cofactors has to occur within the cytoplasm concomitant with folding. Consequently, cofactor-containing proteins must be secreted through the TAT pathway.

A limitation in the use of the protein secretion, and specifically of the TAT export pathway, for commercial protein production has been that the amount of protein that can be exported in this manner is low. In other words, the overall protein flux through the TAT system is substantially lower than that of the sec pathway.

Currently, there is no reliable technology that can be used to screen for increased periplasmic secretion of recombinant proteins, nor is there an optimized TAT-specific leader peptide. However, results obtained from the methods disclosed herein would lead to characterization of optimized leader peptides that can circumvent the slow transit rates typically observed for wild type or native twin-arginine leader sequences. The present invention also enables a thorough and systematic determination on minimal leader sequence requirements for proper and efficient export through the TAT pathway. Moreover, the methods disclosed herein can also identify leader peptides that mediate enhanced protein secretion through other pathways such as the sec pathway.

The present invention thus provides, in one aspect, a method of identifying a leader peptide that directs increased protein export through the Twin Arginine Translocation or TAT pathway by constructing expression cassettes that put mutated candidate TAT-specific leader peptides upstream of a gene encoding a short-lived reporter protein. Such a short lived reporter protein exhibits a decreased half life in the cytoplasm relative to reporter protein molecules that have been exported from the cytoplasm. The short-lived reporter protein can be created, for example, by attaching a cytoplasmic degradation sequence to the gene encoding the reporter protein. In general, mutated leader peptides may be generated by random mutagenesis, error-prone PCR and/or site-directed mutagenesis. The resulting expression cassettes can then be expressed in bacteria, and expression of the reporter protein be measured. Mutated TAT-specific leader peptides expressed in cells that exhibit increased expression of reporter protein are leader peptides that would direct increased protein export through the TAT pathway.

Methods that are well known to those skilled in the art can be used to construct expression cassettes or vectors containing appropriate transcriptional and translational control signals. See for example, the techniques described in Sambrook et al., 200, *Molecular Cloning: A Laboratory Manual* (2nd Ed.), Cold Spring Harbor Press, N.Y. Vectors of the invention include, but are not limited to, plasmid vectors and viral vectors.

In one embodiment of the screening methods described herein, green fluorescent protein (GFP) may be used as a reporter protein. The method takes advantage of the fact that functional, fluorescent green fluorescent protein can only be secreted using a TAT-specific leader peptide. However, the export of green fluorescent protein via a TAT specific leader peptide is inefficient and results in the accumulation of an appreciable amount of precursor protein (green fluorescent protein with the TAT-specific leader) in the cytoplasm. The cytoplasmic green fluorescent protein precursor protein is folded correctly and is fluorescent. As a result, the cells exhibit high fluorescence, which in part is contributed by the cytoplasmic precursor and in part by the secreted, mature green fluorescent protein in the periplasm. The overall high fluorescence of these cells contributes to a high background signal which complicates the isolation of leader peptide mutations that give rise to a higher flux of exported green fluorescent protein.

To circumvent this problem, a short-lived version of green fluorescent reporter protein may be used. This short-lived version is rapidly degraded within the bacterial cytoplasm. Fusion of the SsrA sequence AANDENYALAA (SEQ ID NO:119), for example, to the C-terminal of green fluorescent protein targets the protein for degradation by the ClpXAP protease system (Karzai et al., 2000). As a result, the half-life of green fluorescent protein in the cytoplasm is reduced from several hours to less than 10 min, resulting in a significant decrease in whole cell fluorescence.

It was shown that, when the short lived green fluorescent protein was fused to a wild-type TAT-specific leader peptide, a low level of cell fluorescence was observed because most of the protein was degraded prior to export from the cytoplasm. It was contemplated that mutations in the TAT-specific leader peptide may cause faster and more efficient export that rescues the short lived green fluorescent protein from degradation in the cytoplasm. As a result, folded green fluorescent protein would be accumulated in the periplasm, leading to higher cell fluorescence. Therefore, libraries of mutant TAT-specific leader peptides were constructed by either random mutagenesis (error-prone PCR) or nucleotide directed mutagenesis. These mutant leader peptides were then screened for their ability to mediate enhanced protein secretion and rescue the short-lived green fluorescent protein from degradation in the cytoplasm, thereby leading to increased fluorescence of the bacteria. Clones exhibiting higher fluorescence were then isolated by flow cytometry.

One particular feature of the present invention is that the genetic screen described herein results in periplasmic-only accumulation of active reporter protein. The mutated leader peptides direct folded green fluorescent reporter protein to the periplasm where the fluorescent protein remains active. However, due to the presence of the SsrA C-terminal degradation peptide, virtually all cytoplasmic green fluorescent protein is degraded. The resulting cells glow green in a halo-type fashion due to the presence of periplasmic-only green fluorescent protein. In contrast, TAT-dependent export of green fluorescent protein that lacks the SsrA sequence would lead to green fluorescent protein accumulation in both the cytoplasm and the periplasm, resulting in substantial background signal that makes cell-based screening of GFP fluorescence impossible.

In addition to green fluorescent protein, various other reporter proteins can be used in the methods of the present invention. A person having ordinary skill in this art could readily isolate mutant leader peptides that result in higher levels of reporter protein expression in the periplasm in a number of ways. In one example, if the reporter is an antibiotic resistance enzyme (e.g., β-lactamase), then mutant leader peptides can be isolated by selecting on increasing concentrations of antibiotic. In another example, if the reporter is an immunity protein to a toxin (e.g., colicins), mutant leader peptides can be isolated by selecting for resistance to toxin. In another example, if the reporter protein is a transport protein such as maltose binding protein, export of the transport protein is used to complement chromosomal mutants. In another example, the chromogenic or fluorogenic substrate of a reporter enzyme (e.g. alkaline phosphatase) can be used to score for colonies that produce higher levels of the enzyme in the bacterial periplasm.

There are a number of research and industrial uses for the screening system described herein. Examples of these research and industrial uses include, but are not necessarily limited to, the following:

(1) Bio-Production of Proteins: The secretion of several proteins via the TAT pathway has been reported to be a relatively slow and inefficient process. Therefore, the need for improved export must be realized in order to make the TAT pathway a feasible platform for high-level production of high-value recombinant protein products. Using the genetic screens outlined herein, optimized TAT leader peptides have been isolated and tested for their ability to rapidly export recombinant proteins of interest. The recombinant proteins are thus secreted into the periplasmic space or the growth medium in a functional and soluble form, alleviating problems associated with inclusion bodies and simplifying recovery. Furthermore, since proteins are folded and accumulate in the cytoplasm prior to TAT-dependent export, this export system will likely result in higher levels of active product accumulation within the host cell, thus maximizing the efficiency of the recombinant expression system.

(2) In High-Throughput Screening Platforms: The present invention can be applied in the development of technologies that capitalize on TAT-dependent export for combinatorial library screening and protein engineering applications. For example, improved cytoplasmic folding of disulfide bond containing proteins (e.g., antibodies, eucaryotic enzymes) can be assayed by fusion to optimized leader peptides that export the folded proteins of interest to the periplasm where it can be easily accessed by FACS-based or phage-based screening protocols. The amount of active protein detected in the periplasm would be a quantitative indicator of the efficiency of folding in the cytoplasm.

(3) In Drug Discovery Programs: Homologues of some TAT proteins have been identified in pathogenic bacteria such as *Mycobacterium tuberculosis* and *Helicobacter pylori* as well as *Pseudomonas sp*. This indicates that some proteins belonging to this translocation system may be potential new targets for antibacterial agents. Using the processes outlined herein, a large number of compounds can easily be screened for inhibition of TAT-dependent secretion. Furthermore, the presence of certain proteins in multicopy derived from genomic libraries or random deletion of genes from the genome can be tested using this process to identify novel enhancers/suppressors of the TAT secretion process in bacteria, thereby providing a more general approach to developing antimicrobials.

The present invention of identifying and using leader peptides that direct enhanced protein secretion in bacteria is not limited to the TAT pathway. The methods disclosed herein are equally applicable for identifying leader peptides that direct enhanced protein secretion through other secretion pathways as described above. Signal sequences which promote protein translocation to the periplasmic space of Gram-negative bacterial are well-known to one of skill in the art. For example, the *E. coli* OmpA, Lpp, LamB, MalE, PelB, and StII leader peptide sequences have been successfully used in many applications as signal sequences to promote protein secretion in bacterial cells such as those used herein, and are all contemplated to be useful in the practice of the methods of the present invention. A person having ordinary skill in this art can readily employ procedures well-known in the art to construct libraries of mutated leader sequences and expression cassettes that incorporate these mutated leader peptides, and screen these leader peptides according the methods described herein.

The present invention also relates to secretion of partially or filly folded cytoplasmic proteins with disulfide bonds. The formation of disulfide bonds is essential for the correct folding and stability of numerous eukaryotic proteins of importance to the pharmaceutical and bioprocessing industries. Correct folding depends on the formation of cysteine-cysteine linkages and subsequent stabilization of the protein into an enzymatically active structure. However, numerous studies have demonstrated that multiple disulfide bond-containing proteins cannot be expressed in active form in bacteria. Disulfide bond formation is blocked in the reducing environment of the cytoplasm of a cell due to the presence of thioredoxin reductase or reduced glutathione.

Thus, the production of technologically important proteins with four or more disulfide bonds is costly and complicated and must rely either on expression in higher eukaryotes that provide a favorable environment for the formation of disulfide bonds or refolding from inclusion bodies (Hockney, 1994; Georgiou and Valax, 1996). For example, tissue plasminogen activator (tPA) is currently produced in bacteria inclusion bodies. In typical procedures, the proteins are released from inclusion bodies using a variety of chaotropic agents, then isolated and refolded by employing reducing agents. Generally, refolding results in low yields of biologically active material.

The process of secretion disclosed herein provides an efficient method of producing complex eukaryotic proteins with multiple disulfide bonds. These disulfide bonds form from specific orientations to promote correct folding of the native protein. Multiple disulfide bonds resulting from improper orientation of nascently formed proteins in the cell lead to misfolding and loss or absence of biological activity. In contrast, biologically-active polypeptide-containing multiple disulfide bonds produced according to the instant invention will be correctly folded; disulfide bonds will form to provide a tertiary and where applicable, quaternary structure leading to a molecule with native functional activity with respect to substrates and/or catalytic properties. The proteins produced by the method disclosed herein are correctly folded and biologically active without the need for reactivation or subsequent processing once isolated from a host cell.

The most immediate problem solved by the methods disclosed herein is that proteins with multiple disulfide bonds can now be exported to the periplasm in a fully folded and therefore active conformation. Complex proteins containing multiple disulfide bonds can be folded in the cytoplasm with the assistance of a full complement of folding accessory factors that facilitate nascent polypeptides in reaching their native conformation. The folded proteins are then secreted into the periplasmic space or the growth medium in a functional and soluble form, thus alleviating problems associated with inclusion bodies and simplifying recovery. In addition, active recombinant proteins accumulate simultaneously in two bacterial compartments (cytoplasm and periplasm), leading to greater overall yields of numerous complex proteins which previously could not actively accumulate in both compartments concurrently.

Thus, the present invention provides a method of producing at least one biologically-active heterologous polypeptide in a cell. A leader peptide that directs protein export through the Twin Arginine Translocation pathway may be placed upstream of a gene encoding the heterologous polypeptide in an expression cassette. The expression cassette can be expressed in a cell, wherein the heterologous polypeptide is produced in a biologically-active form. Generally, the heterologous polypeptide is secreted from the bacterial cell, is isolatable from the periplasm or the culture supernatant of the bacterial cell, or is an integral membrane protein. The heterologous polypeptide produced by this method can be a mammalian polypeptide such as tissue plasminogen activator, pancreatic trypsin inhibitor, an antibody, an antibody fragment or a toxin immunity protein. The heterologous polypeptide may be a polypeptide in native conformation, a mutated polypeptide or a truncated polypeptide.

Using a cell that has an oxidizing cytoplasm, the above method can produce a heterologous polypeptide containing from about 2 to about 17 disulfide bonds. This method may also produce two heterologous polypeptides that are linked by at least one disulfide bond. Preferably, the leader peptide comprises a sequence of SEQ ID NOs:25–46, 120–128 or a peptide homologous to SEQ ID NOs:25–46, 120–128. Representative cells which are useful in this method include E. coli trxB mutants, E. coli gor mutants, or E. coli trxB gor double mutants such as E. coli strain FA113 or E. coli strain DR473.

The present invention also provides a series of putative TAT-specific leader peptides, which can be identified by a bioinformatics search from E. coli, cloned and examined for functional activities. Thus, the present invention encompasses isolated leader peptides that direct protein secretion and export through the Twin Arginine Translocation pathway. Representative leader peptides comprise sequences of SEQ ID NOs:25–46, 120–128. Moreover, the present invention includes isolated TAT leader peptides that are homologous to SEQ ID NOs:25–46, 120–128.

The present invention also provides a method of identifying a leader peptide that directs increased protein export by constructing expression cassettes that put mutated leader peptides upstream of a gene encoding a short-lived reporter protein. The short-lived reporter protein can be created by attaching a cytoplasmic degradation sequence to the gene encoding the reporter protein. Representative cytoplasmic degradation sequences include SEQ ID NO:119, PEST, or sequences recognized by LON, clPAP, clPXP, Stsh and HslUV. The cytoplasmic degradation sequences are attached to either the N- or C-terminal of the reporter protein. In general, reporter proteins that can be used include fluorescent proteins, an enzyme, a transport protein, an antibiotic resistance enzyme, a toxin immunity protein, a bacteriophage receptor protein and an antibody.

Mutated leader peptides can be generated, for example, by random mutagenesis, error-prone PCR or site-directed mutagenesis, as well as other methods known to those of skill in the art. The resulting expression cassettes can then be expressed in bacteria, and expression of the reporter protein measured. Mutated leader peptides expressed in cells that exhibit increased expression of reporter protein comprise leader peptides that would direct increased protein export in bacteria. This screening method is capable of identifying leader peptides that direct protein secretion through the general secretory (Sec) pathway, the signal recognition particle (SRP)-dependent pathway, the YidC-dependent pathway or the twin-arginine translocation (Tat) pathway.

In another aspect of the present invention, there is provided a method of increasing export of heterologous polypeptide in bacteria. Expression cassettes are constructed that put mutated leader peptides identified according to the methods of the invention upstream of a coding sequence encoding a heterologous polypeptide of interest. These expression cassettes can then be expressed in bacteria.

The present invention also provides a method of screening for a compound that inhibits or enhances protein export in bacteria. A leader peptide that directs protein export in bacteria may be placed upstream of a gene encoding a short-lived reporter protein in an expression cassette. The expression cassette may then be expressed in bacteria in the presence or absence of a test compound. Increased expression of the reporter protein measured in the presence of the test compound indicates the compound enhances protein export, whereas decreased expression of the reporter protein measured in the presence of the compound indicates the compound inhibits protein export. Construction and examples of short-lived reporter protein are described above.

The present invention also provides a method of identifying a leader peptide that directs increased protein export through the Twin Arginine Translocation pathway by constructing expression cassettes that put mutated leader peptides specific for the Twin Arginine Translocation pathway upstream of a coding sequence encoding a short-lived reporter protein. Construction and examples of short-lived reporter protein are described above. The mutated leader peptides can be generated by random mutagenesis, error-prone PCR or site-directed mutagenesis. The resulting expression cassettes can then be expressed in bacteria, and expression of the reporter protein measured. Mutated leader peptides expressed in cells that exhibit increased expression of reporter protein comprise leader peptides that would direct increased protein export through the Twin Arginine Translocation pathway. Examples of mutated leader peptides comprise sequences of SEQ ID Nos: 120–128.

In another aspect of the present invention, there is provided a method of increasing export of heterologous polypeptide through the Twin Arginine Translocation pathway. Expression cassettes may be constructed that put mutated leader peptides identified according to the methods disclosed herein upstream of a gene encoding a heterologous polypeptide of interest. These expression cassettes may then be expressed in bacteria. Examples of mutated leader peptides comprise sequences of SEQ ID NOs:120–128.

The present invention also provides a method of screening for a compound that inhibits or enhances protein export through the Twin Arginine Translocation pathway. A leader peptide specific for the Twin Arginine Translocation pathway may be placed upstream of a gene encoding a short-lived reporter protein in an expression cassette. The expression cassette may then be expressed in bacteria in the presence or absence of a test compound. Increased expression of the reporter protein measured in the presence of the test compound indicates the compound enhances protein export, whereas decreased expression of the reporter protein measured in the presence of the compound indicates the compound inhibits protein export through the Twin Arginine Translocation pathway. Construction and examples of short-lived reporter protein are described above.

As used herein, "polypeptide" or "polypeptide of interest" refers generally to peptides and proteins having more than about ten amino acids. The polypeptides are "heterologous," meaning that they are foreign to the host cell being utilized, such as a human protein produced by a CHO cell, or a yeast polypeptide produced by a mammalian cell, or a human polypeptide produced from a human cell line that is not the native source of the polypeptide. Examples of a polypeptide of interest include, but are not limited to, molecules such as renin, a growth hormone (including human growth hormone), bovine growth hormone, growth hormone releasing factor, parathyroid hormone, thyroid stimulating hormone, lipoproteins, α1-antitrypsin, insulin A-chain, insulin β-chain, proinsulin, thrombopoietin, follicle stimulating hormone, calcitonin, luteinizing hormone, glucagon, clotting factors (such as factor VIIIC, factor IX, tissue factor, and von Willebrands factor), anti-clotting factors (such as Protein C, atrial naturietic factor, lung surfactant), a plasminogen activator, (such as human tPA or urokinase), mammalian trypsin inhibitor, brain-derived neurotrophic growth factor, kallikreins, CTNF, gp120, anti-HER-2, human chorionic gonadotropin, mammalian pancreatic trypsin inhibitor, antibodies, antibody fragments, protease inhibitors, therapeutic enzymes, lymnphokines, cytokines, growth factors, neurotrophic factors, insulin chains or pro-insulin, immunotoxins, bombesin, thrombin, tumor necrosis factor-α or β,.enkephalinase, a serum albumin (such as human serum albumin), mullerian-inhibiting substance, relaxin A-chain, relaxin B-chain, prorelaxin, mouse gonadotropin-associated peptide, a microbial protein (such as β-lactamase), Dnase, inhibin, activin, vascular endothelial growth factor (VEGF), receptors for hormones or growth factors, integrin, protein A or D, rheumatoid factors, neurotrophic factors (such as neurotrophin-3, -4, -5, or -6), or a nerve growth factor (such as NGF-β), cardiotrophins (cardiac hypertrophy factor) (such as cardiotrophin-1), platelet-derived growth factor (PDGF), fibroblast growth factor (such as α FGF and β FGF), epidermal growth factor (EGF), transforming growth factor (TGF) (such as TGF-α, TGF-β1, TGF-β2, TGF-β3, TGF-β4, or TGF-β5), insulin-like growth factor-I and -II, des(1–3)-IGF-I (brain IGF-I), insulin-like growth factor binding proteins, CD proteins (such as CD-3, CD-4, CD-8, and CD-19), erythropoietin, osteoinductive factors, bone morphogenetic proteins (BMPs), interferons (such as interferon-α, -β, and -γ), colony stimulating factors (CSFs) (e.g., M-CSF, GM-CSF, and G-CSF), interleukins (Ils) (such as IL-1 to IL-10), superoxide dismutase, T-cell receptors, surface membrane proteins, decay accelerating factor, viral antigens such as a portion of the AIDS envelope, transport proteins, homing receptors, addressins, regulatory proteins, antigens such as gp120(IIIb), or derivatives or active fragments of any of the peptides listed above. The polypeptides may be native or mutated polypeptides, and preferred sources for such mammalian polypeptides include human, bovine, equine, porcine, lupine, and rodent sources, with human proteins being particularly preferred.

The following examples are given for the purpose of illustrating various embodiments of the invention and are not meant to limit the present invention in any fashion.

EXAMPLE 1

Bioinformatics Search for TAT-Specific Leader Peptides

Putative TAT leader peptides were found using the Protein-Protein "BLAST" search engine available through the National Center for Biotechnology Information website. The following search strings were entered: SRRRFLK (SEQ ID NO:2), SRRXFLX (SEQ ID NO:3), TRRXFLX (SEQ ID NO:4), SRRXXLK (SEQ ID NO:5), SRRXXLA (SEQ ID NO:6), TRRXXLK (SEQ ID NO:7), TRRXXLA (SEQ ID NO:8), SRRXXLT (SEQ ID NO:9), SRRXXIK (SEQ ID NO:10), SRRXXIA (SEQ ID NO:11), SRRXFIX (SEQ ID NO:12), SRRXFMK (SEQ ID NO:13), SRRXFVK (SEQ ID NO:14), SRRXFVA (SEQ ID NO:15), SRRQFLK (SEQ ID NO:16), RRXFLA (SEQ ID NO:17), and RRXFLK (SEQ ID NO:18). Searches were done for short, nearly exact matches and then screened for only those matches occurring within the first 50 residues of the protein while still maintaining the twin-arginines. The first 100 residues of each leader peptide were then examined by "SignalP", a program for detecting Sec pathway leader peptides and cleavage sites (Nielsen et al., 1997). The final list of putative TAT leader peptides is shown in Table 1. These peptides were cloned and examined for their abilities to direct secretion of a reporter protein, GFP-SsrA, through the TAT pathway.

Bacterial Strains and Growth Conditions:

Cells were always grown at 37° C., either on solid LB agar or in liquid LB media and with appropriate antibiotics. Chloramphenicol (Cm) was used at the concentration of 50 µg/mL. The strain XL1-Blue (recA1 endA1 gyrA96 thi-1 hsdR17 supE44 relA1 lac [F'proAB lacI$^q$ZΔM15 Tn10 (Tet$^r$)]) (Stratagene) was used for cloning purposes. For expression, the high-copy pBAD18-Cm constructs were transformed into the strains MC4100-P (MC4100 pcnB1) and B1LK0-P (MC4100 ΔtatC pcnB1).

Plasmids and Oligonucleotides:

Each putative leader peptide DNA sequence was first subcloned into pKKGS (DeLisa et al, 2002), which is based on the low-copy pBAD33 plasmid (Guzman et al., 1995). Standard methods were used to amplify DNA and Qiagen kits were used for all DNA purification steps. Each leader peptide gene was first PCR amplified from XL1-Blue genomic DNA using a forward primer that contained a SacI cleavage site and a reverse primer that contained an XbaI cleavage site. Forward primers were designed to incorporate at least the first 18 nucleotides of the leader peptide. All forward primers contained the sequence (5'-GCGATGGAGCTCTTAAAGAG-GAGAAAGGTC-3', SEQ ID NO:19) followed by the start codon and leader peptide sequence from the desired gene. Similarly, all reverse primers contained the sequence (5'-GCGATGTCTAGA-3', SEQ ID NO:20). Reverse primers were designed such that exactly six amino acid residues beyond the predicted leader peptide cleavage site would be incorporated into the plasmid. The resulting 58 primers are shown in Tables 2 and 3. All PCR products were gel purified and digested using SacI and XbaI and finally cloned into the SacI and XbaI sites of pKKGS. All plasmid constructs were confirmed by sequencing.

Similar constructs were made using the high-copy plasmid pBAD18-Cm (Guzman et al., 1995). Briefly, signal sequence-GFP-SsrA fusion constructs were digested from pBAD33 using SacI and HindIII and cloned into the identical sites of pBAD18-Cm. In the case of the HybO leader peptide, the HybO-GFP-SsrA fusion was cut with SacI and SphI and cloned into pBAD18-Cm. As before, all plasmid constructs were confirmed by sequencing.

Subcellular Localization of Proteins:

Cells were pelleted by centrifugation at 5000×g, resuspended in 1 ml of cell fractionation buffer (30 mM Tris-HCl, pH 8.0, 20% (w/v) sucrose, 1 mM $Na_2EDTA$), and incubated at 25° C. for 10 min. The cells were again centrifuged at 5000×g, the supernatant discarded, and the pellet resuspended in 133 μl of ice-cold 5 mM $MgSO_4$. After 10 min on ice, the cells were centrifuged at full speed, and the supernatant was retained as the periplasmic fraction. The pellet was resuspended in 250 μl of PBS and sonicated for 30 seconds. The cells were centrifuged at full speed and the supernatant was retained as the cytoplasmic fraction.

Western Blotting Analysis:

Western blotting was according to Chen et al. The following primary antibodies were used: monoclonal mouse anti-GFP (Clontech) diluted 1:5000, monoclonal rabbit anti-DsbC (gift from John Joly, Genentech) diluted 1:10,000 and monoclonal rabbit anti-GroEL (Sigma) diluted 1:10,000. The secondary antibody was 1:10,000 goat anti-mouse-HRP conjugate and goat anti-rabbit-HRP conjugate. Membranes were first probed with anti-GFP and anti-DsbC antibodies and, following development, were stripped in TBS/2% SDS/0.7 M β-mercaptoethanol. Stripped membranes were re-blocked and probed with anti-GroEL antibody.

FACS Screening of Putative Leader Peptide:

To express the leader peptide-GFP-SsrA constructs, overnight (o/n) cultures of MC4100-P and B1LK0-P containing each of the 30 plasmids were grown in LB media as described above. Single colonies were grown overnight in 2 mL of media. Five hundred μl of each o/n culture were used to inoculate 10 mL of media. After 1 h shaking at 37° C., cells were induced with arabinose to a final concentration of 0.02%. Following four more hours of incubation at 37° C., 1 mL samples were harvested and centrifuged at 2500×g for 5 min. Cell pellets were resuspended in 1 mL of PBS. Of that, 5 μL were added to 1 mL fresh PBS and analyzed by the Becton-Dickenson FACSort.

Thirty putative TAT leader peptides were screened in a genetic screen as described previously (DeLisa et al. 2002). With this genetic screen, a leader peptide that directs GFP through the TAT pathway would be fluorescent in $tatC^+$ cells (MC4100-P) but non-fluorescent in $tatC^-$ cells (B1LK0-P) since tatC is absolutely necessary for TAT export. By contrast, a leader peptide that directed GFP to the periplasm via the Sec pathway would be non-fluorescent in both types of cells. Of note is the use of E. coli strains containing a mutation in pcnB1, which lowers the copy number of those plasmids (such as pBAD18-Cm) that contain the pBR322 replicon. Thus pBAD18-Cm, which is normally a high copy vector, is only present at approximately 5–10 copies per cell in pcnB1 mutants. This system proved optimal for use with the TAT pathway genetic screen.

The FACS analysis for the pBAD18-Cm constructs are shown in Table 4 (a list of arithmetic mean fluorescence values). Importantly, the FACS data for the pBAD18-Cm constructs shows that six leader peptides (BisZ, NapA, NapG, YaeI, YgfA, and YggJ) gave inconclusive GFP export through the TAT pathway (low signal in both wt and tatC mutant celsi) while at least 17 (AmiC, DmsA, FdnG, FdoG, FhuD, HyaA, HybA, NrfC, SufI, TorA, WcaM, YacK, YahJ, YdcG, YdhX, YfhG, and, YnfE) are capable of exporting GFP via the TAT pathway. Five constructs (YagT, YcbK, YcdB, YedY, and YnfF) displayed very high fluorescence means in both MC4100-P and B1LK0-P. It should also be noted that the higher mean fluorescence signals seen for some of the constructs in the tatC mutant (B1LK0-P) reflected emission from only a small population of highly fluorescent cells while the bulk of the cell population was non-fluorescent. In contrast, the high mean fluorescence of the tatC+ cells (MC4100-P) was indicative of a shift in the fluorescence emission throughout the population.

TABLE 1

E. coli. TAT-Specific Leader Peptides

| # | Gene | Sequence | SEQ ID NO. |
|---|------|----------|------------|
| 1 | WcaM | MPFKKLSRRTFLTASSALAFLHTPFARAL | 25 |
| 2 | NrfC | MTWSRRQFLTGVGVLAAVSGTAGRVVAK | 26 |
| 3 | YahJ | MKESNSRREFLSQSGKMVTAAALFGTSVPLAHAA | 27 |
| 4 | HyaA | MNNEETFYQAMRRQGVTRRSFLKYCSLAATSLGLGA GMAPKLAWAL | 28 |
| 5 | YacK | MQRRDFLKYSVALGVASALPLWSRAVFAA | 29 |
| 6 | YcbK | MDKFDANRRKLLALGGVALGAAILPTPAFAT | 30 |
| 7 | YfhG | MRHIFQRLLPRRLWLAGLPCLALLGCVQNHNK | 31 |
| 8 | YcdB | MQYKDENGVNEPSRRRLLKVIGALALAGSCPVAHAQ | 32 |
| 9 | AmiA | MSTFKPLKTLTSRRQVLKAGLAALTLSGMSQAIAK | 33 |
| 10 | YedY | MKKNQFLKESDVTAESVFFMKRRQVLKALGISATAL SLPHAAHAD | 34 |
| 11 | FhuD | MSGLPLISRRRLLTAMALSPLLWQMNTAHAA | 35 |
| 12 | HybA | MNRRNFIKAASCGALLTGALPSVSHAAA | 36 |

TABLE 1-continued

E. coli TAT-Specific Leader Peptides

| # | Gene | Sequence | SEQ ID NO. |
|---|------|----------|------------|
| 13 | YdcG | MDRRRFIKGSMAMAAVCGTSGIASLFSQAAFAA | 37 |
| 14 | SufT | MSLSRRQFIQASGIALCAGAVPLKASAA | 38 |
| 15 | YagT | MSNQGEYPEDNRVGKHEPHDLSLTRRDLIKVSAATAATAVVYPHSTLAA | 39 |
| 16 | YdhX | MSWIGWTVAATALGDNQMSFTRRKFVLGMGTVIFFTGSASSLLAN | 40 |
| 17 | HybO | MTGDNTLIHSHGINRRDFMKLCAALAATMGLSSKAAAE | 41 |
| 18 | YnfF | MMKIHTTEALMKAEISRRSLMKTSALGSLALASSAFTLPFSQMVRAA | 42 |
| 19 | DmsA | MKTKIPDAVLAAEVSRRGLVKTTAIGGLAMASSALTLPFSRIAHAV | 43 |
| 20 | YnfE | MSKNERMVGISRRTLVKSTAIGSLALAAGGFSLPFTLRNAAAAV | 44 |
| 21 | FdoG | MQVSRRQFFKICAGGMAGTTAAALGFAPSVALAE | 45 |
| 22 | AmiC | MTDYASFAKVSGQISRLLVTQLRFLLLGRGMSGSNTAISRRRLLQGAGAMWLLSVSQVSLAA | 46 |
| 23 | YggJ | twin-arginine consensus motif: RRRGFLT | 47 |
| 24 | YgfA | twin-arginine consensus motif: QRRRALT | 48 |
| 25 | BisZ | twin-arginine consensus motif: TRREFIK | 49 |
| 26 | NapA | twin-arginine consensus motif: SRRSFMK | 50 |
| 27 | NapG | twin-arginine consensus motif: GRRRFLR | 51 |
| 28 | FdnG | twin-arginine consensus motif: SRRQFFK | 52 |
| 29 | YaeI | twin-arginine consensus motif: SRRRFLQ | 53 |

*Amino acids highlighted in gray constitute the twin-arginine consensus motif.

TABLE 2

Forward Primers And Their Melting Temperature For Each of The 29 TAT-Specific Leader Peptides

| Name | $T_m$ (° C.) | Sequence | SEQ ID NO. |
|------|--------------|----------|------------|
| WcaM for2 | 57.0 | GCGATGGAGCTCTTAAAGAGGAGAAAGGTCATGCCATTTAAAAAACTCTCCCGA | 54 |
| NrfC for | 57.5 | GCGATGGAGCTCTTAAAGAGGAGAAAGGTCATGACCTGGTCTCGTCGC | 55 |
| YahJ for2 | 57.5 | GCGATGGAGCTCTTAAAGAGGAGAAAGGTCATGAAAGAAAGCAATAGC | 56 |
| HyaA for2 | 55.8 | GCGATGGAGCTCTTAAAGAGGAGAAAGGTCATGAATAACGAGGAAACATTTTACCAG | 57 |
| YggJ for | 62.5 | GCGATGGAGCTCTTAAAGAGGAGAAAGGTCGTGGGGAGACGACGCGGA | 58 |
| YacK for | 51.8 | GCGATGGAGCTCTTAAAGAGGAGAAAGGTCATGCAACGTCGTGATTTC | 59 |
| NapG for | 57.5 | GCGATGGAGCTCTTAAAGAGGAGAAAGGTCATGTCCCGGTCAGCGAAA | 60 |
| YcbK for | 52.9 | GCGATGGAGCTCTTAAAGAGGAGAAAGGTCATGGACAAATTCGACGCT | 61 |
| YfhG for | 48.9 | GCGATGGAGCTCTTAAAGAGGAGAAAGGTCATGCGACACATTTTTCAA | 62 |
| YcdB for2 | 52.9 | GCGATGGAGCTCTTAAAGAGGAGAAAGGTCATGCAGTATAAAGATGAAAACGG | 63 |
| AmiA for | 47.5 | GCGATGGAGCTCTTAAAGAGGAGAAAGGTCATGAGCACTTTTAAACCA | 64 |
| B1971 for2 | 51.0 | GCGATGGAGCTCTTAAAGAGGAGAAAGGTCATGAAAAAGAATCAATTTTTAAAAGAATC | 65 |
| FhuD for | 54.2 | GCGATGGAGCTCTTAAAGAGGAGAAAGGTCATGAGCGGCTTACCTCTT | 66 |
| YgfA for | 55.6 | GCGATGGAGCTCTTAAAGAGGAGAAAGGTCATGATTCGGCAACGTCGT | 67 |

TABLE 2-continued

Forward Primers And Their Melting Temperature For Each of The 29 TAT-Specific Leader Peptides

| Name | $T_m$ (°C.) | Sequence | SEQ ID NO. |
|---|---|---|---|
| BisZ for2 | 50.7 | GCGATGGAGCTCTTAAAGAGGAGAAAGGTCATG ATCAGGGAGGAAGTT | 68 |
| HybA for2 | 60.3 | GCGATGGAGCTCTTAAAGAGGAGAAAGGTCGTG AACAGACGTAATTTTATTAAAGCAGCCTC | 69 |
| YdcG for | 48.6 | GCGATGGAGCTCTTAAAGAGGAGAAAGGTCATG GATCGTAGACGATTT | 70 |
| Sufi for | 57.1 | GCGATGGAGCTCTTAAAGAGGAGAAAGGTCATG TCACTCAGTCGGCGT | 71 |
| YagT for | 55.8 | GCGATGGAGCTCTTAAAGAGGAGAAAGGTCATG AGCAACCAAGGCGAA | 72 |
| B1671 for | 51.5 | GCGATGGAGCTCTTAAAGAGGAGAAAGGTCATG TCATGGATAGGGTGG | 73 |
| B2997 for | 48.8 | GCGATGGAGCTCTTAAAGAGGAGAAAGGTCATG ACTGGAGATAACACC | 74 |
| NapA for | 51.8 | GCGATGGAGCTCTTAAAGAGGAGAAAGGTCATG AAACTCAGTCGTCGT | 75 |
| B1588 for2 | 58.9 | GCGATGGAGCTCTTAAAGAGGAGAAAGGTCATG ATGAAAATCCATACCACAGAGGCG | 76 |
| DmsA for | 53.1 | GCGATGGAGCTCTTAAAGAGGAGAAAGGTCATG AAAACGAAAATCCCTGATG | 77 |
| YalE for | 56.3 | GCGATGGAGCTCTTAAAGAGGAGAAAGGTCATG TCCAAAAATGAACGAATGGTG | 78 |
| FdnG for | 56.8 | GCGATGGAGCTCTTAAAGAGGAGAAAGGTCATG GACGTCAGTCGCAGA | 79 |
| FdoG for | 55.5 | GCGATGGAGCTCTTAAAGAGGAGAAAGGTCATG CAGGTCAGCAGAAGG | 80 |
| AmiC for | 60.8 | GCGATGGAGCTCTTAAAGAGGAGAAAGGTCATG ACAGATTATGCGTCTTTCGCTAAAGTT | 81 |
| YaeI for | 58.5 | GCGATGGAGCTCTTAAAGAGGAGAAAGGTCATG ATTTCACGCCGCCGA | 82 |

TABLE 3

Reverse Primers And Their Melting Temperature For Each of The 29 TAT-Specific Leader Peptides

| Name | $T_m$ (°C.) | Sequence | SEQ ID NO. |
|---|---|---|---|
| WcaM rev2 | 59.7 | GCGATGTCTAGAGCTTTGTCGGGCGGG AAG | 83 |
| NrfC rev3 | 56.2 | GCGATGTCTAGAATTGATATTCAACGTT TTCGCCAC | 84 |
| YahJ rev3 | 60.1 | GCGATGTCTAGATAGGGTGCCAGCTAC CGC | 85 |
| HyaA rev2 | 57.4 | GCGATGTCTAGAGCGCGGTTTGTTCTCC AG | 86 |
| YggJ rev | 357.3 | GCGATGTCTAGATACGCGCCCGATATG GTT | 87 |
| YacK rev4 | 56.5 | GCGATGTCTAGATAACGTTGGGCGTTCT GC | 88 |
| NapG rev2 | 65.1 | GCGATGTCTAGAGCGCAACCGCACGCC AGA | 89 |
| YcbK rev2 | 56.9 | GCGATGTCTAGAGCGTGGGGTAGAGAG TGT | 90 |
| YfhG rev2 | 53.4 | GCGATGTCTAGACGTATCAATGGCTGG CTT | 91 |
| YcdB rev2 | 52.1 | GCGATGTCTAGACGCACTTTGCGTTTTT TG | 92 |

TABLE 3-continued

Reverse Primers And Their Melting Temperature For Each of The 29 TAT-Specific Leader Peptides

| Name | $T_m$ (°C.) | Sequence | SEQ ID NO. |
|---|---|---|---|
| AmiA rev4 | 47.8 | GCGATGTCTAGATTTTAAAAGTTCGTCTTTGG | 93 |
| B1971 rev2 | 50.2 | GCGATGTCTAGAAAACCAGCTAAGCAGATC | 94 |
| FhuD rev4 | 53.3 | GCGATGTCTAGAATTGGGATCAATAGCCGC | 95 |
| YgfA rev2 | 50.6 | GCGATGTCTAGAGAATACAGCGACCGTATG | 96 |
| BisZ rev2 | 52.3 | GCGATGTCTAGATTTACCGCCCTTCTCTTC | 97 |
| HybA rev2 | 62.5 | GCGATGTCTAGATGGCGGGCGGTTTTCAGC | 98 |
| YdcG rev2 | 48.6 | GCGATGTCTAGAGGCAATATCAGAATCTGC | 99 |
| SufI rev2 | 63.2 | GCGATGTCTAGACGGTTGCTGTTGCCCGGC | 100 |
| YagT rev2 | 62.3 | GCGATGTCTAGAAGCTGCCGGAACGCTTGC | 101 |
| B1671 rev2 | 51.3 | GCGATGTCTAGACTTTTCTTGCCTCGTGTT | 102 |
| B2997 rev2 | 55.5 | GCGATGTCTAGAAACCGATTCGGCCATCTC | 103 |
| NapA rev2 | 60.3 | GCGATGTCTAGACTGACCAACAACGGCGCG | 104 |
| B1588 rev4 | 56.9 | GCGATGTCTAGATTCTACCGGAGCCTCTGC | 105 |
| DmsA rev | 55.5 | GCGATGTCTAGATGGAATGGCGCTATCGAC | 106 |
| YnfE rev | 57.5 | GCGATGTCTAGATTTTTCGCGGGCCTGTTG | 107 |
| FdnG rev | 54.9 | GCGATGTCTAGATAATTTGTAGTTTCGCGCCTG | 108 |
| FdoG rev | 54.7 | GCGATGTCTAGACAGTTTATACTGCCGGGTTTC | 109 |
| AmiC rev | 61.6 | GCGATGTCTAGACGCCACGACCTGGCTGAC | 110 |
| YaeI rev | 58.9 | GCGATGTCTAGAGCTCGTGGCTATCGTCGC | 111 |

TABLE 4

FACS Screening of Putative Leader Peptides

| Leader Peptide | MC4100-P | B1LK0-P (% Cells) | Protein Export |
|---|---|---|---|
| AmiC | 9 | 2 (95) | + |
| BisZ | 2 | 3 (100) | |
| DmsA | 287 | 11 (95) | +++ |
| FdnG | 1 | 2 (100) | ND |
| FdoG | 44 | 2 (97.1) | + |
| FhuD | 10 | 2 (99.5) | + |
| HyaA | 90 | 3 (96.6) | ++ |
| HybA | 411 | 2 (95.6) | +++ |
| HybO | N/A | N/A | |
| NapA | 1 | 2 (100) | |
| NapG | 6 | 7 (95) | |
| NrfC | 43 | 9 (95) | + |
| SufI | 337 | 3 (96.6) | +++ |
| TorA | 203 | 34 (100) | +++ |
| WcaM | 96 | 6 (99) | ++ |
| YacK | 72 | 13 (100) | ++ |
| YaeI | 2 | 2 (100) | |
| YagT | 436 | 235 (95) | − |
| YahJ | 684 | 3 (100) | +++ |
| YcbK | 367 | 97 (95) | + |
| YcdB | 514 | 356 (95) | − |
| YdcG | 59 | 27 (100) | ++ |
| YdhX | 18 | 4 (95) | + |
| YedY | 73 | 35 (95) | − |
| YfhG | 36 | 7 (95) | + |
| YgfA | 8 | 3 (100) | |
| YggJ | 1 | 2 (100) | |
| YnfE | 24 | 8 (100) | + |
| YnfF | 203 | 101 (95) | − |

Arithmetic fluorescent means from FACS data of pBAD18-Cm::leader peptide-GFP-SsrA constructs in MC4100-P and B1LK0-P cells. Data for the B1LK0-P cells were calculated from all the cells (% cells shown) except the small population of highly fluorescent cells.

EXAMPLE 2

Bacterial Strains and Plasmids Construction

All strains and plasmids used in the following examples are listed in Table 5. *E. coli* strain XL1-Blue (recA1 endA1 gyrA96 thi-1 hsdR17 supE44 relA1 lac [F' proAB lacI$^q$ZΔM15Tn10 (Tet$^r$)]) was used for all experiments unless otherwise noted. *E. coli* XL1-Blue tatB and XL1-Blue tatC were made using pFAT24 (Sargent et al. 1999) and pFAT166 (Bogsch et al, 1998) respectively according to established procedure (Bogsch et al., 1998). Strains were routinely grown aerobically at 37° C. on Luria-Bertani (LB) media and antibiotic supplements were at the following concentrations: ampicillin, 100 μg ml$^{-1}$, chloramphenicol, 25 μg ml$^{-1}$.

The plasmids constructed in the following examples were based on pBAD33 (Guzman et al., 1995) and were made using standard protocols Sambrook et al., 2000). Plasmid pGFP was constructed by cloning the GFPmut2 variant (Crameri et al., 1996) using the primers GFPXbaI (5'-GC-GATGTCTAGAAGTAAAGG AGAAGAACTTTTCACT-3', SEQ ID NO:112) and GFPHindIII (5'-GCGATGAAGCT-TCTATTTGTATAGTTCATCCAT-3', SEQ ID NO:113) which introduced unique restriction sites of XbaI and HindIII at the 5' and 3' ends respectively of the 716-bp gfpmut2 gene and enabled cloning of this sequence into XbaI-HindIII digested plasmid DNA. Plasmid pGFPSsrA was made similarly using the primers GFPXbaI and GFPSsrA (5'-GCGAT-GAAGCTTGCATGCTTAAGCT-GCTAAAGCGTAGTTTTCG TCGTTTGCTGCGTCGACTTTGTATAGT-TCATCCATGCC-3', SEQ ID NO:114) to introduce the unique SsrA recognition sequence. Plasmid pTorAGFP and pTorAGFPSsrA were made by PCR amplification of *E. coli* genomic DNA using primers TorASacI (5'-GCGATGGAAT-TCGAGCTCTTAAAGAGGAGAAAGGTCAT-GAACAATAACGATCT CTTTCAG-3', SEQ ID NO:115) and TorAXbaI (5'-GCGATGTCTAGAAGCGTCAGTCGC-CGCTTGCGCCGC-3', SEQ ID NO:116) to generate a 138-bp torA cDNA with unique SacI and XbaI restriction sites at the 5' and 3' ends respectively. This sequence was then inserted into SacI-XbaI digested pGFP or pGFPSsrA plasmid DNA. All plasmids constructed in this study were confirmed by sequencing.

TABLE 5

Bacterial Strains And Plasmids

| Strain or plasmid | Relevent genotype/phenotype | Source |
| --- | --- | --- |
| *E. coli* strains | | |
| XL1-Blue | | Stratagene |
| XLtatB | XL1-Blue with tatB deletion | This study |
| XLtatC | XL1-Blue with tatC deletion | This study |
| Plasmids | | |
| pFAT24 | pMAK705 carrying tatB deletion allele | (Sargent et al., 1999) |
| pFAT166 | pMAK705 carrying tatC deletion allele | (Bogsch et al., 1998) |
| pGFP | Signal sequenceless GFP in pBAD33 | This study |
| pGFPssrA | Signal sequenceless GFP tagged with C-terminal ssrA tag in pBAD33 | This study |
| pTorAGFP | TorA leader peptide fused to GFP in pBAD33 | This study |
| pTorAGFPssrA | TorA leader peptide fused to ssrA-tagged GFP in pBAD33 | This study |
| pB6::GFP | Clone B6 leader cloned into pGFP | This study |
| pB7::GFP | Clone B7 leader cloned into pGFP | This study |
| pE2::GFP | Clone E2 leader cloned into pGFP | This study |
| pTorAR30Q | pTorAGFP with R12Q mutation in leader | This study |
| pTorAR30QGFPssrA | pTorAGFPSsrA with R12Q mutation in leader | This study |

EXAMPLE 3

Flow Cytometric Analysis

Overnight cultures of XL1-Blue cells harboring GFP-based plasmids were subcultured into fresh LB medium with chloramphenicol and induced with 0.2% arabinose in mid-exponential phase growth. After 6 h, cells were washed once with PBS and 5 μl washed cells were diluted into 1 ml PBS prior to analysis using a Becton-Dickinson FACSort.

EXAMPLE 4

Generation of torA Combinatorial Libraries

A library of random mutants was constructed by error prone PCR of the torA gene sequence using 3.32 or 4.82 mM $Mg^{2+}$ (Fromant et al., 1995), XL1-Blue genomic DNA and the following primers: torASacI (5'-GCGATGGAATTC-GAGCTCTTAAAGAGGAGAAAGGTCAT-GAACAATAACGATCT CTTTCAG-3') (SEQ ID NO:117) and torAXbaI (5'-GCGATGTCTAGAAGCGTCAGTCGC-CGCTTGCGCCGC-3') (SEQ ID NO:118). To construct libraries with 0.5% error rate, 0.22 mM dATP, 0.20 mM dCTP, 0.34 mM dGTP and 2.36 mM dTTP were used, whereas 0.12 mM dATP, 0.1 mM dCTP, 0.55 mM dGTP and 3.85 mM dTTP were used to construct libraries with 1.5% error rate. Libraries were digested with SacI-XbaI and ligated into pGFPssrA between SacI-XbaI, placing the library upstream of the gfpssrA sequence. Reaction mixtures were electroporated into electrocompetent XL1-Blue cells (Stratagene), and serial dilutions were plated on selective plates to determine the number of independent transformants.

EXAMPLE 5

Library Screening

Transformants were grown at 37° C. in LB medium with chloramphenicol, induced with 0.2% arabinose for 6 h and diluted 200-fold in 1 ml PBS. FACS gates were set based upon FSC/SSC and FL1/FL2. Prior to sorting, the library cell population was labeled with propidium iodide for preferential labeling of non-viable cells. A total of ca. $3\times10^6$ cells were analyzed by flow cytometry and 350 viable cells were collected. The collected solution was filtered, and the filters were placed on LB plates with chloramphenicol. After a 12 hour incubation at 37° C., individual colonies were inoculated into LB with chloramphenicol in triplicate 96-well plates. Following 12 hours of growth at 37° C., cells were similarly subcultured into triplicate 96-well plates containing LB with chloramphenicol and 0.2% arabinose and grown for 6 hours at 37° C. Individual clones were screened via FACS and fluorescent plate reader (Bio-Tek FL600, Bio-Tek Instrument, Winooski, Vt.) for verification of fluorescent phenotype.

EXAMPLE 6

Cell Fractionations

The fraction of periplasmic proteins was obtained by spheroplasting bacteria by lysozyme-EDTA treatment under isotonic conditions according to the procedure of Kaback (1971). Briefly, cells were collected by centrifugation and resuspended to an $OD_{600}$ of 10 in a buffer containing 100 mM Tris-Cl (pH 8.0), 0.5 M sucrose, and 1 mM Na-EDTA. Lysozyme (Sigma) was added to 50 μg/ml, and cells were incubated for 1 h at room temperature to generate spheroplasts. The spheroplasts were pelleted by 15 min of centrifugation at 3,000×g, and the supernatant containing periplasmic proteins was collected for electrophoretic analysis. The pellet containing spheroplasts was resuspended in 10 ml of TE (10 mM Tris-Cl [pH 7.5], 2.5 mM Na-EDTA) and homogenized in a French press cell (Carver) at 2,000 lb/in². To analyze total proteins of untreated cells, direct resuspension in 10 ml of TE followed by subjection to the French press homogenization was performed.

EXAMPLE 7

Screening of Signal Peptide Libraries for Improved Export Phenotypes

The plasmid pTorAGFP contains a gene encoding the TAT-specific leader peptide and the first eight amino acids of the *E. coli* trimethylamine N-oxide reductase (TorA) fused to the FACS optimized GFPmut2 gene (Crameri et al., 1996). The TorA-GFP gene was placed downstream of the arabinose-inducible promoter pBAD. Cells induced with arabinose for 6 hours and analyzed by FACS gave a mean fluorescence intensity (MFL1) above 500 arbitrary units (FIG. 1C). In agreement with previous reports (Santini et al., 2001), cell fractionation by osmotic shock revealed that ca. 40–50% of total fluorescence was located in the periplasm of wild type cells while cytoplasmic GFP accounted for the remaining 50–60% of total fluorescence. In tatB and tatC mutants where the TAT pathway were abolished, greater than 95% of total fluorescence was retained in the cytoplasm, thereby demonstrating that TorA-GFP is exported via the TAT pathway.

A nucleotide sequence encoding a C-terminal SsrA degradation peptide was fused to the TorA-GFP gene. The resulting gene, pTorA-GFP-SsrA, was also placed downstream from a pBAD promoter in the vector pTorAGFPSsrA. As a negative control, GFP without the leader peptide was fused in frame to the SsrA tag and expressed from the plasmid pGFPSsrA. GFP-SsrA-expressing cells showed virtually no appreciable fluorescence intensity, indicating that cytoplasmic SsrA-tagged GFP is degraded almost completely (FIG. 1A). Cells expressing TorA-GFP-SsrA were ca. 8 times more fluorescent compared to GFP-SsrA expressing cells (FIG. 1B). Expression of TorA-Gfp-SsrA in tatB and tatC mutant cells only led to background fluorescence.

Error prone PCR (Fromant et al., 1995) was used to generate libraries of random mutants of the TorA leader peptide. Three libraries with expected mutation frequencies of 0.5, 1.5 or 3.5% nucleotide substitutions were constructed. The mutated TorA leader peptides were ligated upstream of the GFP-SsrA sequence in pGFPSrA. Transformation of E. coli resulted in libraries consisting of between $10^6$ and $10^7$ independent transformants. Sequence analysis of 20 randomly selected clones confirmed the presence of randomly distributed mutations within the TorA leader peptide.

Figure 2:
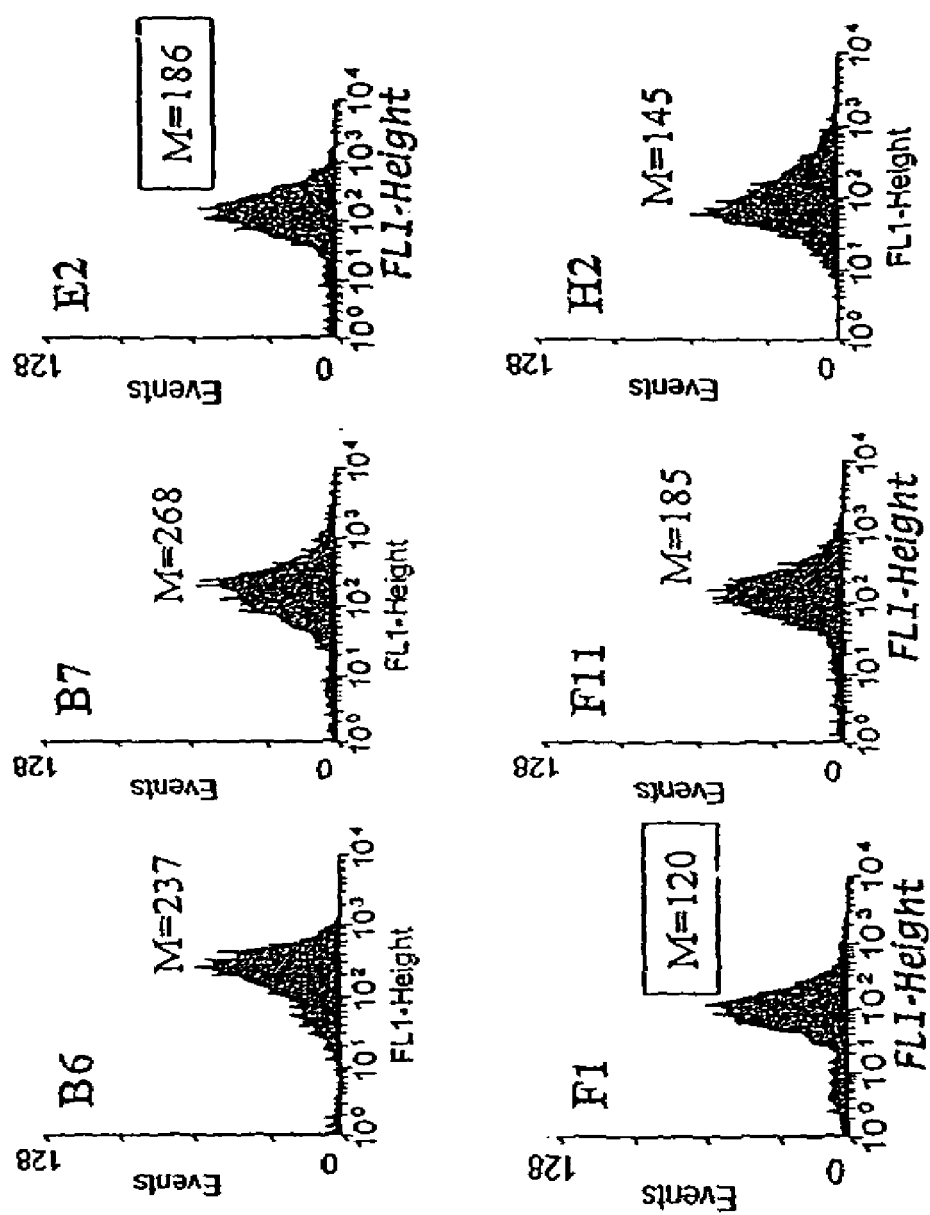
FIG. 2 shows green fluorescent protein fluorescence in 6 different clones that exhibit increased Tat-dependent export due to mutated TorA leader peptides.

FACS-based screening of the three libraries resulted in isolation of a total of six clones, 2 from the higher error rate library and four from the lower error rate libraries. All six clones exhibited higher cell fluorescence relative to the parental TorA-Gfp-SsrA construct (FIG. 2). The increase in the fluorescence level was between 3 and 6-fold relative to what is obtained with the wild type leader peptide. Back transformation of these clones into strains XL1-Blue or DHB4 resulted in maintained fluorescence levels, thus indicating that the increased fluorescence was conferred by the respective plasmids and was not due to an unrelated mutation in the host cell. When the plasmids were transformed into tatb or tatC cells the cell fluorescence was abolished, as would be expected for a process that is dependent on the TAT export system.

Figure 3:
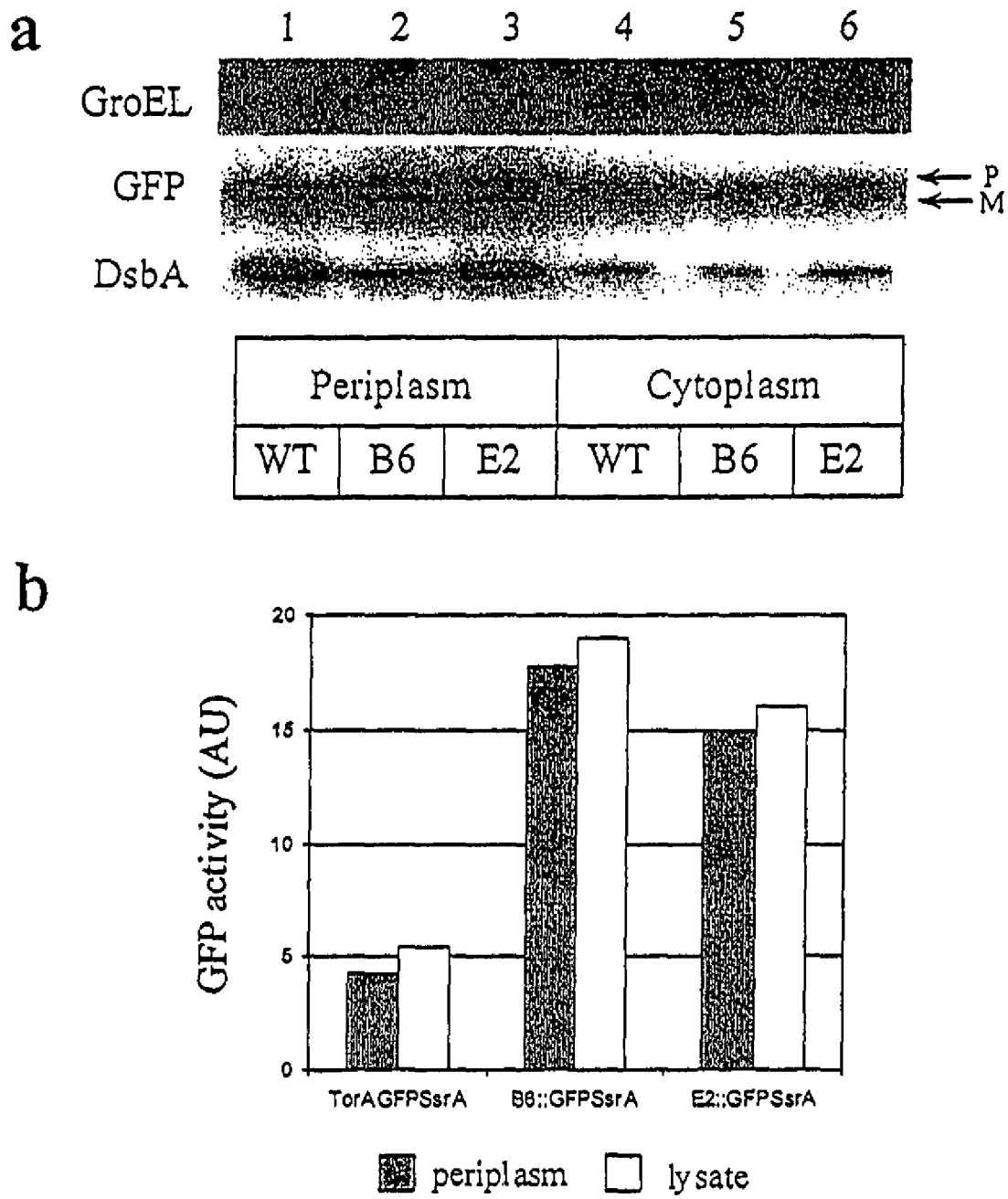
FIG. 3 shows periplasmic green fluorescent protein accumulation in the B6 and E2 clones.

Representative Western blots indicate that periplasmic GFP accumulation by cells expressing the B6 and E2 clones was significantly increased relative to those expressing wild type construct (lanes 1–3, FIG. 3). Furthermore, there was virtually no detectable GFP protein in the cytoplasmic fractions. This was because the presence of the SsrA tag resulted in degradation of the protein. Also shown in FIG. 3 were Western bands of two fractionation marker proteins, the cytoplasmic marker GroEL and the periplasmic marker DsbA. The absence of GroEL in the periplasmic fraction and the high level of DsbA in periplasmic fractions confirm that cell fractionation was successful.

Data on the distribution of fluorescence in the cytoplasmic and periplasmic fractions for two mutant TorA leader peptides are shown in FIG. 3B. Nearly identical results were observed for the remaining four clones (B7, F1, F11 and H2). The sequences of the six clones were determined and indicated that in all cases either one or two single residue mutations were sufficient to alter the observed export dynamics. In general, these mutations occur within or in close proximity to the conserved S/T-R-R-x-F-L-K (SEQ ID NO: 1) consensus motif (Table 6).

Figure 4:
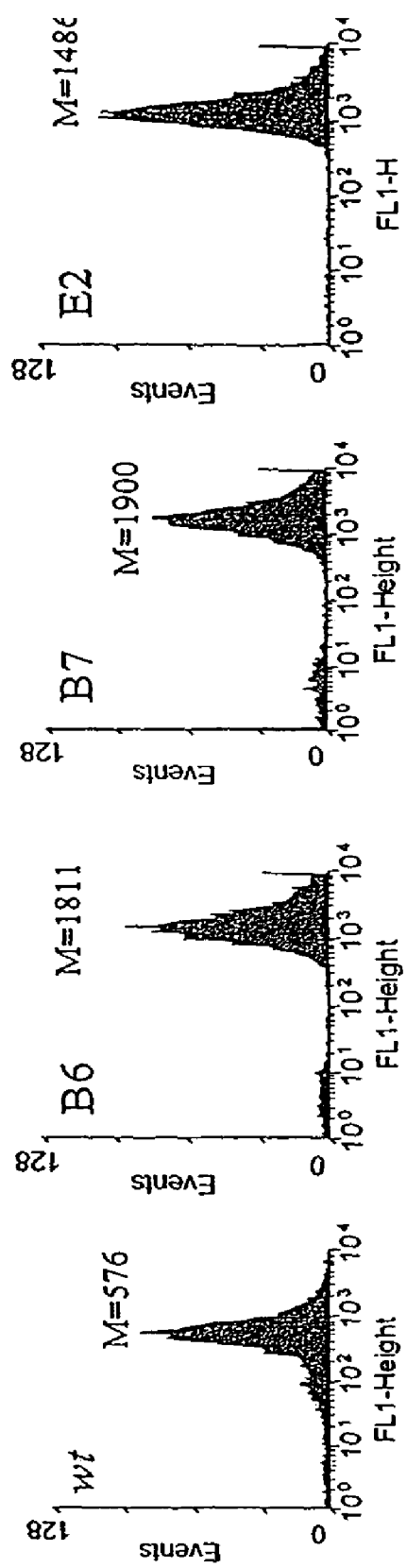
FIG. 4 shows increased green fluorescent protein fluorescence in cells expressing the wild type construct, the B6, B7 or E2 construct fused to untagged, proteolytically stable green fluorescent protein.

It was confirmed that the six mutant TorA leader peptides confer increased GFP export not only when the protein is tagged with the SsrA tag but also for the untagged, proteolytically stable GFP (FIG. 4). This increase in fluorescence was due to the increased periplasmic flux of folded GFP protein. Similar results were observed for the remaining clones fused to GFP.

Figure 5:
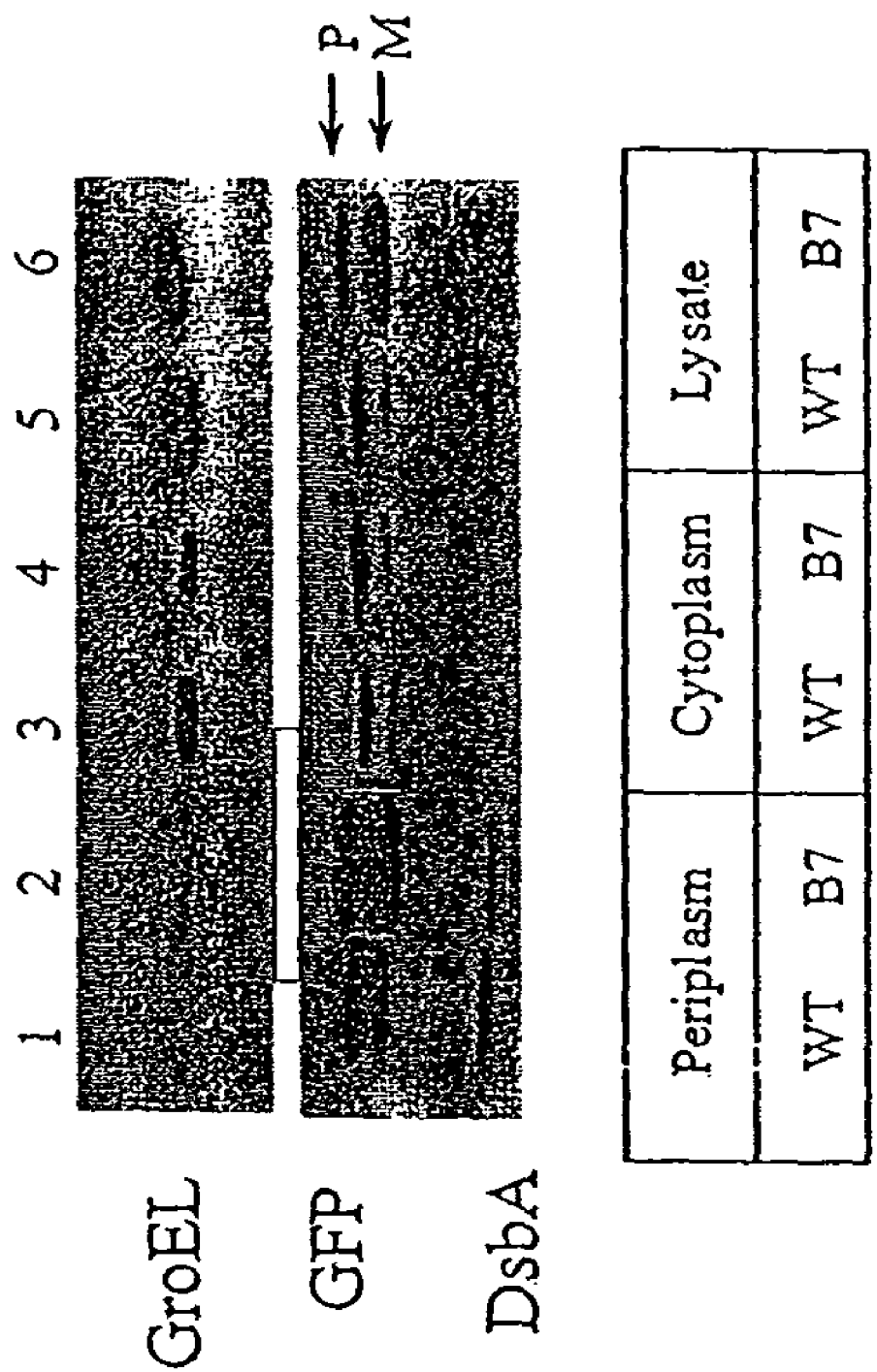
FIG. 5 shows western blot of green fluorescent protein in the periplasm (lanes 1–2), cytoplasm (lanes 3–4) and whole cell lysate (lanes 5–6) of cells expressing the wild type construct (lanes 1,3 and 5) or the B7 clone (lanes 2, 4 and 6). GroEL is a cytoplasmic marker whereas DsbA is a periplasmic marker.

A representative Western blot comparing wild type TorA-GfP and TorAB7-Gfp indicated that cells expressing both constructs accumulated nearly identical levels of cytoplasmic GFP (FIG. 5, lanes 3 and 4). However, the amount of exported GFP was significantly higher in cells expressing the ToAB7-GFP clone (FIG. 5, lanes 1 and 2). Further support of this can be seen in the whole cell lysates. The intense band denoted as mature (M) GFP represents TorA-Gfp chimeric protein that has been processed most likely by signal peptidase I (Berks et al, 2000). Therefore, the intense band corresponding to mature GFP accumulated by the TorAB7-GfP construct signifies substantially more periplasmic processing of GFP relative to wild type TorAGFP cells (FIG. 5, lanes 5 and 6). Similar results were observed for all five remaining clones. As described above, the GroEL and DsbA marker proteins confirm successful cell fractionations.

TABLE 6

Sequences Of Six Clones Exhibiting Increasing TAT-Dependent Secretion

| Clone ID | Amino Acid Sequence | |
|---|---|---|
| Wild type | MNNNDLFQA<u>SRRRFLA</u>QLGGLTVAGMLGPSLLTPRRATAAQAATD | (SEQ ID NO:120) |
| B6 | MNNNDLFQ<u>T</u><u>SRRRLLA</u>QLGGLTVAGMLGPSLLTPRRATAAQAATDA | (SEQ ID NO:121) |
| B7 | MNNNDLFQ<u>T</u><u>SRQRFLA</u>QLGGLTVAGMLGPSLLTPRRATAAQAATDA | (SEQ ID NO:122) |
| E2 | MNNNDIFQA<u>SRRRFLA</u>QPGGLTVAGMLGPSLLTPRRATAAQAATDA | (SEQ ID NO:123) |
| F1 | MNNNELFQA<u>SRRRFLA</u>QLGGLTVAGMLGPSLLTPRRATAAQAATDA | (SEQ ID NO:124) |
| F11 | MNNNDLFQ<u>T</u><u>TRRRFLA</u>QLGGLTVAGMLGPSLLTPRRATAAQAATDA | (SEQ ID NO:125) |
| H2 | MNNNDSFQ<u>T</u><u>SRRRFLA</u>QLGGLTVAGMLGPSLLTPRRATAAQAATDA | (SEQ ID NO:126) |

Twin arginine consensus motif is indicated by underlined amino acids; first 8 residues of mature TorA protein are indicated by italics; mutations in TorA leader peptide are indicated by emboldened letters.

EXAMPLE 8

Secretion of Folded Recombinant Proteins Containing Multiple Disulride Bonds Through the Twin Arginine Translocation Export Pathway One embodiment of the methods disclosed herein comprises use of a fusion between a TAT-specific leader peptide and a heterologous polypeptide of interest. For example, TAT-specific leader peptide TorA may be fused to alkaline phosphatase (TorA-PhoA fusion). Alkaline phosphatase (PhoA) contains two disulfide linkages that are consecutive in the primary sequence so that they are normally incapable of forming in the cytoplasm of *E. coli* strains having reducing environment (e.g. strain DHB4). Since the TAT pathway requires folded or at least partially folded substrates, TAT-dependent secretion of PhoA in DHB4 cells would be blocked due to the accumulation of unfolded PhoA in the cytoplasm.

Hence, there is a need to change the cytoplasm into an oxidizing state for secretion through the TAT pathway. Normally, the bacterial cytoplasm is maintained in a reduced state due to the presence of reducing components such as glutathione and thioredoxins that strongly disfavors the formation of disulfide bonds within proteins. Earlier work by Bessette et al. resulted in the engineering of bacterial strains having a highly oxidizing cytoplasm that allows efficient formation of disulfide bonds (Bessette et al., 1999). As shown in Bessette et al., *E. coli* depends on aerobic growth in the presence of either of the two major thiol reduction systems: the thioredoxin and the glutathione-glutaredoxin pathways. Both the thioredoxins and the glutaredoxins are maintained in a reduced state by the action of thioredoxin reductase (TrxB) and glutathione, respectively. Glutathione is synthesized by the gshA and gshB gene products. The enzyme glutathione oxidoreductase, the product of the gor gene, is required to reduce oxidized glutathione and complete the catalytic cycle of the glutathione-glutaredoxin system.

In a trxB null mutant, stable disulfide bonds can form in normally secreted proteins, such as alkaline phosphatase, when they were expressed in the cytoplasm without a signal sequence. The two thioredoxins were oxidized in the trxB mutant and served as catalysts for the formation of disulfide bonds. Disulfide bond formation was found to be even more efficient in double mutants defective in both the thioredoxin (trxB) and glutathione (gor or gshA) pathways. Double mutants, trxB gor or trxB gshA, grow very poorly (doubling time ~300 min) in the absence of exogenous reductant such as DTT and accumulate suppressor mutations in the alkyl hydroperoxidase (ahpC) gene. The resulting ahpC* allele allows efficient growth in normal (non-reducing media) without compromising the formation of disulfide bonds in the cytoplasm. Thus trxB, gor ahpC* mutant strains (such as *E. coli* DR473 or FA113) exhibit the ability to support disulfide bond formation in the cytoplasm and also can grow equally well as the corresponding wild-type strain DHB4 in both rich and minimal media.

In the present example, DHB4 cells expressing TorA-PhoA were found to exhibit almost undetectable alkaline phosphatase activity levels while DR473 cells expressing TorA-PhoA showed extremely high PhoA activity levels. Fractionation experiments confirmed that as much as 50% of the measured PhoA activity in cell lysates were attributed to periplasmic accumulation.

Since the major catalyst of disulfide bond formation is a periplasmic protein, DsbA, which oxidizes thiols in newly synthesized and translocated proteins, it was next determined whether the disulfide bonds were formed in the cytoplasm and secreted intact to the periplasm. The TorA-PhoA construct was expressed in an *E. coli* dsbA mutant, strain DR473 dsbA::kan. A comparison of PhoA activity in the dsbA mutant versus the isogenic DR473 parental strain revealed nearly identical activity levels in whole cell lysates. This result demonstrates that oxidation of the PhoA protein is completed in the cytoplasm, and stable disulfide bonds are able to transverse the inner membrane as the protein is directed from the cytoplasm into the periplasmic space (Table 9).

In order to measure the extent of folding necessary for substrate compatibility with the TAT secretion pathway, eukaryotic model proteins with increasingly complex patterns of disulfide bond formation were tested. The TorA leader peptide was fused to a truncated version of tissue plasminogen activator (vtPA) consisting of the kringle 2 and protease domains with a total of nine disulfides (TorA-vtPA), or to a heterodimeric 2610 anti-digoxin antibody fragment with 5 disulfide bonds including an interchain disulfide linkage (TorA-Fab). DR473 cells expressing TorA-vtPA and TorA-Fab showed remarkably high levels of activities in cell lysates for each of the expressed proteins relative to DHB4 cells expressing identical constructs. Activities in DHB4 lysates were virtually undetectable in all cases except for vtPA. Fractionation experiments further confirmed that significant portion (30–50%) of the overall activities for each of the proteins was found in the periplasmic fraction.

In conclusion, these results show efficient secretion of disulfide linked proteins can occur via the Tat pathway but only in host cells that are able to fold these proteins into their native conformation. Low background levels of active tPA in the periplasm of DHB4 cells suggests that this protein is able to at least partially fold in a reducing cytoplasm. The resulting folded proteins with multiple disulfide bonds are then secreted into the periplasm as an active homo-(alkaline phosphatase) or heterodimer (2610 antibody fragment).

EXAMPLE 9

Demonstration of Export of Multidisulfide Proteins by the Bacterial Twin-Arginine Translocator An examination was carried out to determine whether the formation of disulfide bonds in the cytoplasm of trxB gor aphC mutants was sufficient to render proteins competent for export via the Tat pathway. This was shown to be the case for two model proteins, namely PhoA and Fab fragment raised against digoxin (Fab). PhoA consists of two polypeptide chains with a total of two disulfide bonds that are required for folding and enzymatic activity while Fab is comprised of two non-identical chains (each with two intermolecular disulfide bonds) linked together by an intermolecular disulfide bond. Normally, the formation of disulfide bonds in these proteins occurs following export into the oxidizing environment of the periplasmic space. However, in the analysis, it was demonstrated that proteins with multiple disulfides can be exported via the Tat system after they have first folded in an oxidizing cytoplasm and further, that the transporter mechanistically requires that the substrate be folded properly for periplasmic localization.

A. Procedures

Bacterial Strains, Growth and Induction Conditions:

The bacterial strains and plasmids used are described in Table 7. Strains DHBA and DRA were obtained by P1 transduction of the dsbA::kan1 allele from JCB571 (MC1000 phoR zih12::Tn10 dsbA::kan) into *E. coli* strains DHB4 and DR473, respectively. Strain DØD was obtained by P1 transduction of tatB::kan allele from MCMTA (MC4100 tatB::kan) into *E. coli* strain DR473. Strains FUDDY was obtained by P1 transduction of the tatC::spec allele from BUDDY (MC4100 tatC::spec) into *E. coli* strain FA 113. *E. coli* strain XL1-Blue (recA1 endA1 gyrA96 thi-1 hsdR17 supE44 relA1 lac [F' proAB lac$^q$ZDM15 Tn10 (Tet$^r$)]) was used for cloning and plasmid propagation. For phosphatase assays, cells were subcultured from overnight cultures into minimal M9 medium [M9 salts with 0.2% glucose, 1 µg/ml vitamin B1, 1 mM MgSO$_4$, 50 µg/ml 18 amino acids (excluding methionine and cysteine)] at a 100-fold dilution, and then incubated at 37° C. For Fab studies, cells were subcultured from overnight cultures into fresh LB medium (5% v/v) and then incubated at 30° C. Growth was to mid-log phase (OD$_{600}$~0.5) and induction of both alkaline phosphatase and Fab was accomplished by addition of IPTG to a final concentration of 0.1 mM. Co-expression of DsbC was induced using 0.2% arabinose. Antibiotic selection was maintained for all markers on plasmids at the following concentrations: ampicillin, 100 µg/ml; spectinomycin, 100 µg/ml; and chloramphenicol, 25 µg/ml.

Plasmid Construction:

Plasmid p33RR was constructed by PCR amplification of the *E. coli* torA signal sequence (ssTorA) from *E. coli* genomic DNA using primers TorASacI and TorAXbaI described above. Amplified DNA was digested using SacI and XbaI and inserted into the same sites of pBAD33. Plasmid p33KK was generated identically as p33RR except that mutagenic primer TorAkk (5'-gcgatggagctcttaaagaggagaaaggtcatgaacaataacgatctctttcaggcatcaaagaaacgttttctggcacaactc-3') (SEQ ID NO:129) was used to PCR amplify the torA signal sequence. DNA encoding signal sequence-less phoA (PhoA Δ2–22) was generated by PCR amplification from *E. coli* genomic DNA using primers Phofor (5'-gcgatgtctagacggacaccagaaatgcctgt-3') (SEQ ID NO: 130) and Phorev (5'-gcgatgaagcttttatttcagccccagagcggctt-3') (SEQ ID NO:131). The amplified phoA DNA was digested with XbaI and HindIII and inserted into the same sites of p33RR and p33KK resulting in plasmids p33RRP and p33KKP, respectively. A DNA fragment encoding torA signal sequence (or torA (R11K;R12K) signal sequence) fused in-frame to phoA was amplified from plasmid p33RRP (or p33KKP) using primers TorASacI (or TorAKK) and Phorev. The PCR amplified DNA was digested with BspHI and HindIII and inserted into the NcoI-HindIII sites of pTrc99 resulting in plasmid pRRP (or pKKP). Construction of alkaline phosphatase fusions to alternate signal sequences (e.g. ssFdnG, ssFdoG) was performed identically as described for pTorA-AP. Plasmid pTorA-Fab was constructed by PCR amplification of the anti-digoxin dicistronic Fab gene encoded in pTrc99-Fab (Levy et al., 2001) using primers Fabfor (5'-gctgctagcgaagttcaactgcaacag-3') (SEQ ID NO:132) and Fabrev (5'-gcgatgccggggggctttgttagcagccggatctca-3') (SEQ ID NO: 133) and amplification of torA signal sequence was with primers TorASacI and TorAover (5'-gcgctgttgcagttgaacttcgctagcagcgtcagtcgccgcttg-3') (SEQ ID NO:134). The two PCR products were fused via overlap extension PCR using primers TorASacI and Fabrev. The overlapped product was digested with BspHI and XmaI and inserted into the NcoI and XmaI sites of pTrc99A. All plasmids were confirmed by sequencing.

Cell Fractionations:

The fraction of periplasmic proteins was obtained by ice-cold osmotic shock (Sargent et al., 1998). Specifically, cells were collected by centrifugation and resuspended in buffer containing 30 mM Tris-HCl (pH 8.0), 0.5 M sucrose, 1 mM Na-EDTA and 20 mM iodoacetamide was used to prevent spontaneous activation of alkaline phosphatase. Cells were incubated for 10 min at 25° C. followed by centrifugation for 10 min at 5000×g and 4° C. Pellets were then resuspended in ice-cold 5 mM MgSO$_4$ and kept on ice for 10 min. Cells were centrifuged as before and the supernatant containing periplasmic proteins was collected for electrophoretic analysis. The pellet was resuspended in 10 ml of TE (10 mM Tris-Cl [pH 7.5], 2.5 mM Na-EDTA) and 20 mM iodoacetamide and homogenized in a French press cell at 2,000 lb/in$^2$. To analyze total proteins of untreated cells, direct resuspension in 10 ml of TE and 20 mM iodoacetamide followed by subjection to French press homogenization was performed.

Enzyme Activity Assays:

Cells expressing alkaline phosphatase were induced for 6 h. Samples were harvested, treated with 20 mM iodoacetamide and pelleted by centrifugation. Collected cells were fractionated as described above. Soluble protein was quantified by the Bio-Rad protein assay, using BSA as standard. Activity of alkaline phosphatase was assayed as described previously. Briefly, equal amounts of protein were incubated with 200 µl p-nitrophenyl phosphaste (pNPP; Sigma) solution (1 fast tablet in 100 mM Tris-HCl, pH 7.4) and $\Delta A_{405}$ was measured to determine rate of hydrolysis by alkaline phosphatase in each sample. Fractionation efficiency was monitored using β-galactosidase as a cytoplasmic marker enzyme and was assayed as described previously. Only data from fractionations in which the marker enzyme activities were ≧95% correctly localized were analyzed.

Elisa:

Assays were performed as follows. Ninety-six-well high binding assay plates (Coming-Costar) were coated (100 ul/well) with 4 ug ml$^{-1}$ BSA-digoxin conjugate or with 4 ug ml$^{-1}$ BSA (100 ul/well). Coated plates were blocked overnight at 4° C. with 5% nonfat dry milk in PBS. The presence of anti-digoxin scFv and Fab antibodies was detected using rabbit-anti-mouse IgG (specific to (Fab')$_2$ light chains) diluted 1:2000 followed by goat anti-rabbit IgG (H+L) conjugated with horse radish peroxidase diluted 1:1000. Development was with addition of OPD substrate (Sigma) and the reaction was quenched by addition of 4.5 N H$_2$SO$_4$. Plates were read at 490 nm on a Bio-Tek Instruments microplate reader.

Western Blotting Analysis:

Western blotting was according to Chen et al. (2001). The following primary antibodies were used: rabbit anti-alkaline phosphatase (Rockland) diluted 1:5,000, rabbit anti-tPA diluted 1:5,000, rabbit anti-mouse IgG (specific for (Fab')$_2$ light chains, Pierce) diluted 1:5,000, monoclonal rabbit anti-DsbA and anti-DsbC (gift from John Joly, Genentech) diluted 1:10,000 and monoclonal rabbit anti-GroEL (Sigma) diluted 1:10,000. The secondary antibody was 1:10,000 goat anti-mouse-HRP and goat anti-rabbit-HRP. Membranes were first probed with primary antibodies and, following development, stripped in TBS/2% SDS/0.7 M β-mercaptoethanol. Stripped membranes were re-blocked and probed with anti-DsbA, anti-DsbC and anti-GroEL antibody.

B. A Strategy for Tat-Dependent Export of Multidisulfide Proteins in *E. Coli*

In bacteria the oxidative folding of secreted proteins is catalyzed by the periplasmic enzyme DsbA which is recycled by the integral membrane protein DsbB. In contrast, the thioredoxin and glutaredoxin pathways maintain the cytoplasm as a highly reducing environment, which disfavors cysteine oxidation in proteins. For this reason, host proteins requiring disulfide bonds are exported to the periplasmic compartment, a process facilitated almost exclusively by the Sec pathway in *E. coli*. The export of such proteins by the Tat pathway has been problematic because the Tat pathway normally accepts as substrates proteins that are already folded. Since proteins that contain disulfide bonds in their native state cannot fold in the cytoplasm, these proteins presumably cannot be accepted as substrates for Tat export. Indeed, several earlier studies have demonstrated that proteins requiring disulfide bonds for folding are not exported via the Tat pathway.

It had been established previously and confirmed that PhoA fused to the trimethylamine N-oxide reductase A (TorA) leader peptide, or for that matter other Tat-specific leader peptides, results in negligible alkaline phosphatase activity, indicating lack of export. Therefore, it was reasoned that proper folding, including the formation of disulfide bonds, in the cytoplasm prior to export would permit export via the Tat pathway. To analyze this, the TorA signal sequence was fused to the N-terminus of *E. coli* alkaline phosphatase (AP) devoid of its natural signal sequence. Wild-type *E. coli* cells (DHB4) harboring plasmid pTorA-AP and induced with IPTG (0.1 mM) produced large quantities of cytoplasmic AP as detected by Western blotting. However, there was no detectable AP in the periplasmic fraction of the DHB4 cells. Activity measurements of the same periplasmic fraction confirmed the lack of extracytoplasmic AP. As expected, AP activity in the cytoplasmic fraction of DHB4 cells was almost entirely inactive due to its failure to acquire disulfides bonds in the cytoplasm of this strain. To determine whether the oxidation state of AP was critical for Tat-dependent export, a trxB gor ahpC triple mutant of *E. coli* (strain DR473) was used to express the ssTorA-AP fusion protein. When ssTorA-AP was expressed from plasmid pTorA-AP (0.1 mM IPTG) in strain DR473, about 25% of the total enzymatic activity was found in the periplasmic space. Western blotting confirmed that partitioning of AP had occurred. It should be noted that the quantity of AP in the cytoplasm of DR473 cells was significantly greater than in DHB4 cells, suggesting that misfolded AP is more highly susceptible to cytoplasmic proteolysis.

In support of this notion, it has been reported that the intracellular stability of alkaline phosphatase was decreased in the absence of either one or both of the disulfide bonds. Importantly, β-galactosidase (LacZ) activity in subcellular fractions was measured (see above) and only samples with <5% LacZ activity in the periplasm were analyzed herein. As a secondary control, cross-reaction of the cytoplasmic chaperone GroEL with specific antisera was used as a control for subcellular fractionation. Overall, it was clear that the folding status of AP was the major determinant in the ability to export this protein by the Tat pathway.

C. Export of PhoA is Tat-Specific

It was recently observed that, in the context of certain Tat signals, AP can be exported in a Tat-independent fashion. Therefore, to confirm that export of AP in DR473 was specific to the Tat pathway, a defective TorA signal peptide mutant in which the R11 and R12 arginine residues were replaced with lysines (R11K;R12K) was fused in frame to signal-sequenceless AP to generate plasmid pKK-AP. It is well documented that replacement of the two conserved arginines with a pair of lysines within the Tat consensus motif (S/T-R-R-x-F-L-K) effectively abolishes translocation (Cristobal, et al., 1999). As expected, DHB4 and DR473 cells expressing ssTorA(R11K; R12K)-AP fusion protein were incapable of accumulating periplasmic AP. Importantly, the amount of cytoplasmic AP in DR473 cells was similar irrespective of whether RR or KK was present within the leader peptide. It is noteworthy that ssTorA(R11K;R12K)-AP accumulated in the cytoplasm of DHB4 cells to a much lesser extent than ssTorA-AP in the same cells. One possible explanation is that a proper Tat signal (Arg-Arg) targets even misfolded AP to the cytoplasmic side of the inner membrane. In turn, membrane localization sequesters some of the misfolded enzyme from proteolysis. In contrast, the defective Lys-Lys leader peptide does not properly interact with the Tat machinery and as a result non-targeted AP is more susceptible to cytoplasmic proteolysis. A similar phenomena has been observed in plant thylakoids where the N-terminal presequence on a large, bulky avidin-bound precursor is available for membrane binding and initial recognition by the transport machinery, but the attached avidin signals the machinery that the precursor is an incorrectly configured substrate and thus import is aborted. Consequently, Muser and Theg proposed that the ΔpH/Tat machinery's proofreading mechanism must operate after precursor recognition but before the committed step in transport.

As an independent confirmation that export was Tat-dependent, P1 transduction of DR473 with the tatB::kan allele from strain MCMTA was performed to generate strain DØD (DR473 tatB::kan). As expected, DØD cells expressing ssTorA-AP fusion protein from plasmid pTorA-AP were unable to accumulate AP in the periplasm as evidenced by Western blotting and activity measurements of subcellular fractions. In addition, AP was exported in a Tat-dependent fashion when fused to two different signal sequences from formate dehydrogenase-N (FDH-N) subunit G (ssFdnG) and FDH-O subunit G (ssFdoG). Collectively, these results confirm that the appearance of AP in the periplasm was completely dependent on export via the Tat pathway and that translocation could be accomplished by several different Tat leader peptides.

D, Folding and Oxidation Occurs in the Cytoplasm Prior to Export

To determine whether PhoA oxidation occurred in the cytoplasm prior to translocation, the ssTorA-AP fusion protein was produced in an *E. coli* dsbA null mutant (strains DHBA and DRA). DsbA is the major periplasmic enzyme involved in catalyzing disulfide bond formation in newly synthesized proteins normally secreted by the Sec pathway. As a result, both the DHBA and DRA mutant strains were completely unable to oxidize periplasmic proteins due to a null mutation of dsbA. Unexpectedly, expression of ssTorA-AP from plasmid pTorA-AP (0.1 mM IPTG) in strain DRA resulted in nearly identical periplasmic AP accumulation and activity compared to that obtained using the DR473 dsbA+ strain. Therefore, the accumulation of active AP in the periplasmic compartment was due almost entirely to the export of AP that had already been folded and oxidized in the cytoplasm.

To determine whether this phenomenom was specific to the TorA presequence or a general feature of the Tat export system, 10 known and putative Tat leader peptides were analyzed (Table 8). The 10 signal sequences were fused in frame to signal sequenceless AP, expressed in six different but genetically related backgrounds and assayed for periplasmic AP activity. To establish a baseline for residual periplasmic AP activity, the constructs were all expressed in strain DHA (DHB4 dsbA::kan). Since AP oxidation is prohibited in both the cytoplasm and periplasm of this strain, the total AP activity measured in DHA was found to be negligible for all leader peptide-AP fusions (Table 9). The periplasmic AP activity measured in the remaining 5 strains was normalized to this baseline level. For comparison, the amount of signal-sequenceless AP (Δ2–22) exported in the same strains was measured and found to be negligible in all six backgrounds.

Next, expression of the constructs in wildtype cells (DHB4) resulted in two distinct outcomes: 1) the Tat leaders AmiA, FdnG, FdoG, HyaA, HybA and TorA were unable to export AP when the cytoplasm was reducing; however 2) certain other Tat leader peptides (DmsA, SufI, YacK and YcbK) could direct AP to the periplasm even though disulfide bond formation in the cytoplasm was not possible. This was likely due to Sec-dependent export of AP. As expected, nearly all of the leader peptides were able to direct AP to the periplasm of strain DR473 due in part to the more oxidizing cytoplasm. The notable exceptions were ssAmiA and ssHybA, which were unable to accumulate AP in the periplasm of all the strains tested. Comparison of AP activity found in the periplasm of DR473 versus DRA (DR473 dsbA::kan) confirmed that in the cases of ssFdnG, ssFdoG, ssHyaA and ssTorA, export of AP occurred only after folding and oxidation were accomplished in the cytoplasm. Expression of the constructs in strains having an oxidizing cytoplasm but a defective Tat apparatus (DØD and DUDDY) demonstrated that ssFdnG, ssFdoG and ssTorA directed AP to the periplasm in a Tat-specific fashion. hn contrast, the export of AP directed by ssSufI, ssYacK and ssYcbK was still able to occur in tatB and tatC mutants confirming the earlier DHB4 results and thus the probable use of the Sec pathway. Interestingly, export of AP by ssHyaA was blocked in a tatC mutant but not in a tatB strain, suggesting that in the context of this leader peptide-AP fusion, Tat export could occur without the TatB protein. It should be noted that export of ColV was similarly observed to occur in a tatC-dependent, tatB-independent fashion when fused to ssTorA. The quality of subcellular fractionations performed for all samples reported in Table 9 was confirmed by lacZ activity measurements as well as by protein dot blotting.

Figure 7:
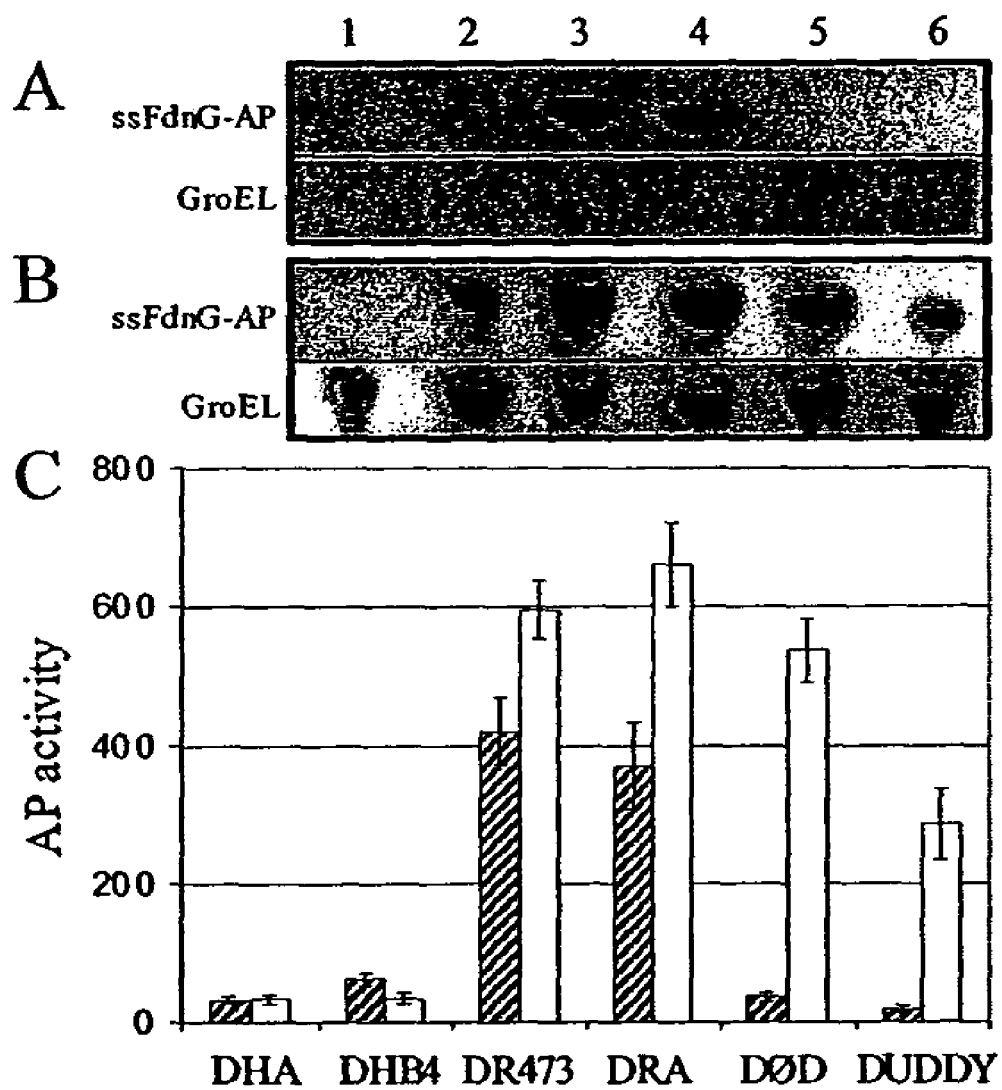
FIG. 7 Shows western blot analysis and AP activity measurements for both periplasmic and cytoplasmic fractions in six genetic backgrounds.

Finally, Western blot analysis and AP activity measurements for both periplasmic and cytoplasmic fractions were performed for the case of ssFdnG-AP expressed in all six genetic backgrounds (FIG. 7). It was noted that the total AP activity (periplasmic and cytoplasmic) found in DR473/pFdnG-AP was nearly identical to the amount of AP measured in the cytoplasm of DR473 expressing the signal-sequenceless version of AP from plasmid pAID135. It is clear from this data that in the context of the ssFdnG leader peptide, AP must be folded and oxidized prior to translocation by the Tat machinery. To the inventors knowledge, this is the first evidence that de novo disulfide bonds formed in the cytoplasm are stably maintained during Tat-dependent membrane translocation. Whether PhoA is translocated as a monomer (~48 kDa) or in its active homodimeric state (~96 kDa) is still unclear, although PhoA is known to fold rapidly into its highly stable, native dimeric state. Moreover, the notion that the large alkaline phosphatase dimer is compatible with the Tat machinery is supported previous studies demonstrating that the 142 kDa FdnGH subcomplex of *E. coli* formate dehydrogenase-N is transported by the Tat system.

EXAMPLE 10

'Hitchhiker' Strategy for Tat-Mediated Export of a Folded Anti-Digoxin Antibody Fragment from the Cytoplasm of *E. coli.*

Figure 6:
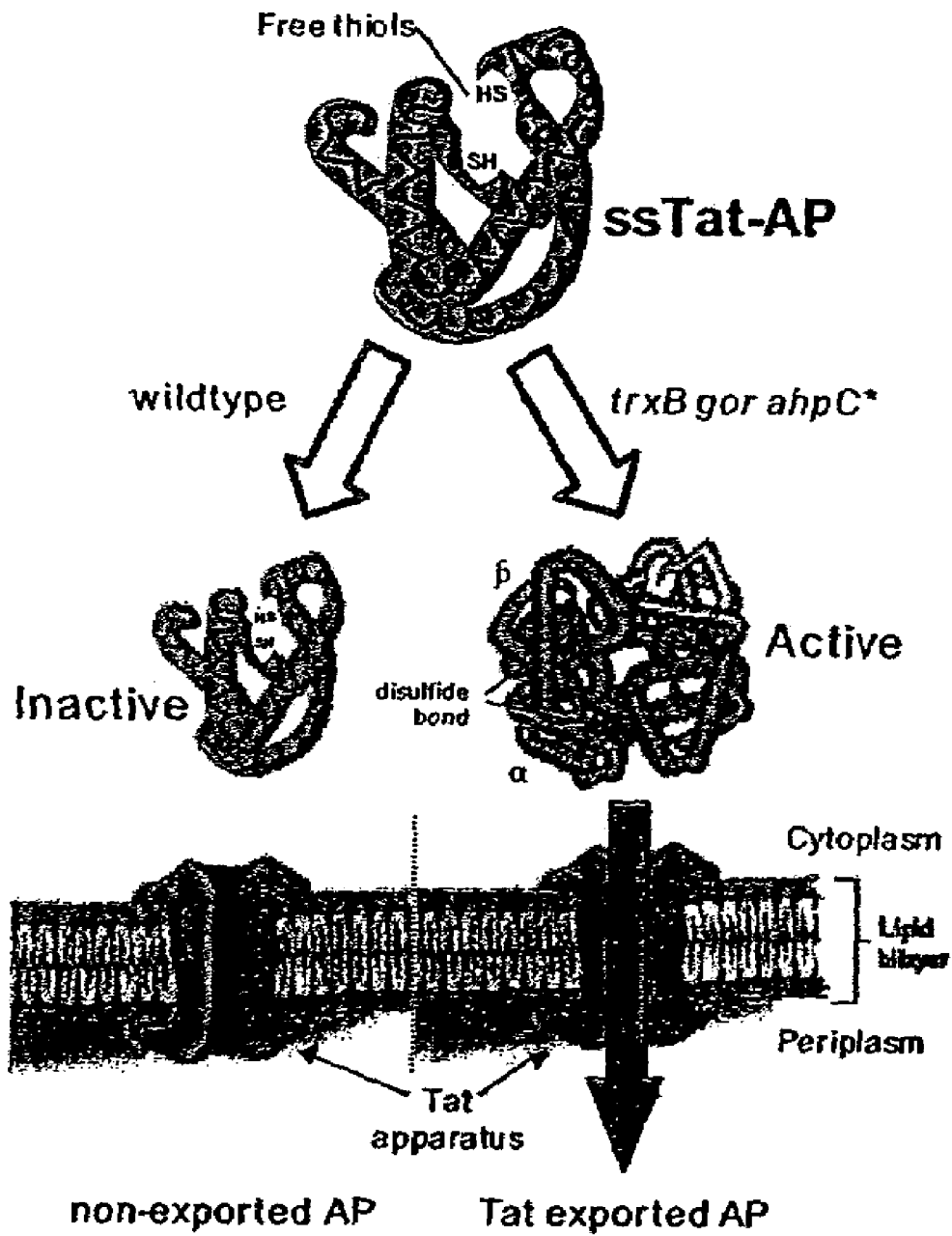
FIG. 6 Shows schematic of export of disulfide linked heterodimer in which only one polypeptide chain was fused to leader peptide.

A considerable portion of the proteins exported by the Tat pathway are enzymes that acquire cofactors in the cytoplasm prior to export and generally function in respiratory or electron transport processes (e.g., *E. coli* trimethlamine N-oxide reductase). The acquisition of cofactors in the cytoplasm requires tertiary structure contacts that occur only after folding has been largely completed. Along these lines, it has been found that membrane targeting and the acquisition of nickel by HybC, the large subunit of the *E. coli* hydrogenase 2, is critically dependent on the export of the small subunit, HybO which contains a Tat-specific leader peptide. The model favored is that the small and large subunits of hydrogenase 2 first form a complex in the cytoplasm and the complex is then targeted to the membrane by virtue of the leader peptide of the small subunit. Analogous to this naturally-occurring complex, it was tested whether a non-physiological heterodimeric antibody fragment could be exported via the Tat translocator when folded properly in the cytoplasm. Surprisingly, it was found that the Tat pathway could also export a disulfide linked heterodimer in which only one polypeptide chain was fused to the TorA leader peptide (see schematic, FIG. 6).

A Fab antibody fragment specific for the cardiac glycoside digoxin was used which consisted of two polypeptide chains, the heavy and light chains, linked together via a disulfide bond. In addition, the heavy and light chains each contained two intra-molecular disulfide bonds. The TorA leader peptide was fused only to the heavy chain ($V_H$-$C_{H1}$) which was co-expressed with the light chain ($V_1$-$C_1$) from a dicistronic operon. In this fashion, the TorA-heavy chain carries the light chain into the periplasm in a 'piggyback' fashion only if the interchain disulfide bridge is formed first in the cytoplasm prior to translocation.

In a mutant strain with an oxidizing cytoplasm (strain DRA) and lacking dsbA, complete Fab protein was exported by the Tat pathway, but only a small fraction of Fab was localized (~15–20%) in the osmotic shock fraction as confirmed by Western blotting. Earlier, it was reported that the folding yield of the anti-digoxin Fab in the cytoplasm is greatly increased by co-expressing a signal-sequenceless version of the periplasmic disulfide isomerase DsbC (ΔssDsbC) or GroEL. In the present analysis, co-expression of ΔssDsbC resulted in a significant increase in the amount of Fab in the periplasm (~50% in the osmotic shock fraction). This may be due to co-expression of chaperones in the cytoplasm increasing the amount of protein competent for export presumably because it improved the yield of folded protein.

Fab was immunologically probed using a primary antibody that recognizes mouse light chain sequences. Therefore, the bands seen confirmed that the light chain was properly recruited by the heavy chain via intermolecular disulfide bond formation and subsequently delivered to the periplasmic space. The localization of the cytoplasmic marker protein GroEL and the periplasmic marker protein DsbC demonstrates that the subcellular fractionation was successful. The Fab protein in the periplasmic fraction of DRA cells was correctly folded and functional as evidenced by its ability to bind the antigen, digoxin in ELISA assays.

As with ssTorA-AP fusions, the appearance of Fab in the osmotic shock fraction was completely abolished in a tatB mutant, when the RR dipeptide in the TorA leader was mutated to KK or in DHB4 cells having a reducing cytoplasm. Moreover, when incubated under conditions that increase the outer membrane permeability (Chen et al., 2001), intact cells expressing Fab antibodies exported into the periplasm via the Tat pathway could be specifically labeled with the fluorescent antigen digoxin-bodipy. The fluorescence of these cells was 5-fold higher than the background fluorescence observed in DHA or DØD control cells. Overall, these results indicate that: (i) the Tat pathway is capable of exporting a fully oxidized Fab across the membrane and (ii) the process is dependent on the assembly of the light and heavy chains and the formation of the intermolecular disulfide within the cytoplasm prior to export. The transport of oxidized, presumably fully folded, Fab molecules into the periplasm provides conclusive evidence for the hitchhiker mode of export suggested previously whereby a polypeptide containing a Tat leader peptide mediates the translocation of a second leaderless polypeptide with which it associates in the cytoplasm.

TABLE 7

Bacterial strains and plasmids used in this study.

| E. coli strain | Relevant phenotype | Source |
|---|---|---|
| DHB4 | MC1000 phoR Δ(phoA) PvuII Δ(malF)3 F' [lacIqZYA pro] | Boyd et al. 1987 |
| DHBA | DHB4 dsbA::kan | This work |
| DR473 | DHB4 ΔtrxB gor552 . . . Tn10Tet ahpC* . . . Tn10Cm(araCP_ara-trxB) | Gift |
| DRA | DR473 dsbA::kan | This work |
| FA113 | DHB4 trxB gor552 . . . Tn10tet^r ahpC* | Gift |
| MC4100 | F-, araD139 Δ(argF-lac) U169 flbB5301 deoC1 ptsF25 relA1 rbsR22 rpsL150 thiA | Casabadan and Cohen 1979 |
| MCMTA | MC4100 tatB::kan | Gift |
| DØD | DR473 tatB::kan | This work |
| BUDDY | MC4100 tatC::spec | Gift |
| FUDDY | FA113 tatC::spec | This work |

TABLE 7-continued

Bacterial strains and plasmids used in this study.

| Plasmid name | Relevant features | Source |
|---|---|---|
| pTrc99A | trc promoter, ColE1 ori, Amp^r | Amersham Pharmacia |
| pTorA-AP | E. coli TorA signal fused to PhoA(Δ2-22) cloned in pTrc99A | This work |
| pKK-AP | as pTorA-AP with R11K; R12K mutation in TorA signal peptide | This work |
| pFdnG-AP | E. coli FdnG signal fused to PhoA(Δ2-22) cloned in pTrc99A | This work |
| pFdoG-AP | E. coli FdoG signal fused to PhoA(Δ2-22) cloned in pTrc99A | This work |
| pAID135 | Signal sequenceless PhoA(Δ2-22) controlled by tac promoter | |
| pTrc99-Fab | Gene encoding anti-digoxin Fab in pTrc99A | |
| pTorA-Fab | E. coli torA signal fused to gene encoding anti-digoxin Fab in Trc99A | This work |
| pKK-Fab | as pTorA-Fab with R11K; R12K mutation in TorA signal peptide | This work |
| pBADdsbC | Gene encoding DsbC with optimized RBS in pBAD33 | |

TABLE 8

Amino acid sequence of leader peptides capable of Tat-dependent export of alkaline phosphatase

| | | |
|---|---|---|
| AmiA* | MSTFKPLKTLTSRRQVLKAGLAALTLSGMSQAIAK | (SEQ ID NO:33) |
| DmsA | MKTKIPDAVLAAEVSRRGLVKTTAIGGLAMASSALTLPFSRIAHAV | (SEQ ID NO:43) |
| FdnG | MDVSRRQFFKICAGGMAGTTVAALGFAPKQALAQ | (SEQ ID NO:127) |
| FdoG | MQVSRRQFFKICAGGMAGTTAAALGFAPSVALAE | (SEQ ID NO:45) |
| HyaA* | MNNEETFYQAMRRQGVTRRSFLKYCSLAATSLGLGAGMAPKIAWAL | (SEQ ID NO:28) |
| HybA | MNRRNFIKAASCGALLTGALPSVSHAAA | (SEQ ID NO:36) |
| SufI | MSLSRRQFIQASGIALCAGAVPLKASAA | (SEQ ID NO:38) |
| TorA | MNNNDLFQASRRRFLAQLGGLTVAGMLGPSLLTPRRATAA | (SEQ ID NO:128) |
| YacK | MQRRDFLKYSVALGVASALPLWSRAVFAA | (SEQ ID NO:29) |
| YcbK | MDKFDANRRKLLALGGVALGAAILPTPAFAT | (SEQ ID NO:30) |

TABLE 9

Periplasmic alkaline phosphatase (AP) activity obtained from fusions between putative Tat signal peptides of E. coli and leaderless E. coli alkaline phosphatase*

| Leader peptide | Periplasmic AP activity |
|---|---|
| pBADΔssdsbC | Gene encoding DsbC(Δ2-20) with optimized RBS in pBAD33 |
| | dsbA |
| | wildtype |

TABLE 9-continued

Periplasmic alkaline phosphatase (AP) activity obtained from fusions between putative Tat signal peptides of *E. coli* and leaderless *E. coli* alkaline phosphatase*

| Leader peptide | Periplasmic AP activity |
|---|---|
| Δ2-20[a] | trxB gor ahpC |
|  | trxB gor ahpC dsbA |
| AmiA[b] | trxB gor ahpC tatB |
| DmsA[c] | trxB gor ahpC tatC |
| FdnG[c] | 1.0 (63) |
|  | 1.3 |
| FdoG | 1.6 |
| HyaA[c] | 1.3 |
|  | 1.3 |
| HybA[b] | 1.2 |
| SufI[c] | nd |
| TorA[c] | nd |
|  | 0.2 |
| YacK[c] | 0.2 |
| YcbK | nd |
|  | 0.1 |
|  | 1.0 (35) |
|  | 3.2 |
|  | 8.0 |
|  | 5.0 |
|  | 3.2 |
|  | 2.1 |
|  | 1.0 (32) |
|  | 1.5 |
|  | 13.1 |
|  | 11.6 |
|  | 0.2 |
|  | 0.2 |
|  | 1.0 (55) |
|  | 1.7 |
|  | 8.1 |
|  | 7.0 |
|  | 0.3 |
|  | 0.2 |
|  | 1.0 (7) |
|  | 1.3 |
|  | 11.0 |
|  | 10.9 |
|  | 3.8 |
|  | 1.2 |
|  | nd |
|  | nd |
|  | 0.2 |
|  | 0.1 |
|  | nd |
|  | 0.1 |
|  | 1.0 (75) |
|  | 4.3 |
|  | 5.4 |
|  | 6.4 |
|  | 3.5 |
|  | 4.1 |
|  | 1.0 (42) |
|  | 1.4 |
|  | 10.4 |
|  | 9.6 |
|  | 0.9 |
|  | 0.4 |
|  | 1.0 (25) |
|  | 3.9 |
|  | 6.1 |
|  | 5.4 |
|  | 7.4 |
|  | 3.2 |
|  | 1.0 (21) |
|  | 2.5 |
|  | 6.6 |
|  | 5.8 |
|  | 6.3 |
|  | 3.0 |

*Relative alkaline phosphatase activity calculated by normalizing activity in sample to activity measured in DHA control strain. Reported values for alkaline phosphatase activity are the average of 3 separate measurements from 2 independent experiments (n = 6). Standard error is less than 10% for all reported data. Values in parenthesis indicate the actual activity measured in the DHA control strain.
[a]Signal-sequenceless AP construct
[b]Values normalized to activity measured in DHA/ssHyaA-AP
[c]Signal sequence carries a c-region positive charge
nd = not detectable

REFERENCES

The following references, to the extent that they provide exemplary procedural or other details supplementary to those set forth herein, are specifically incorporated herein by reference.

Berks et al., *Mol. Microbiol.*, 35:260–274, 2000.
Berks, *Mol. Microbiol.*, 22:393–404, 1996.
Bogsch et al., *J. Biol. Chem.*, 273:18003–18006, 1998.
Bolhuis et al., *J. Biol. Chem.*, 276:20213–20219, 2001.
Bowden and Georgiou, *J. Biol. Chem.*, 265:16760–16766, 1990.
Chanal et al., *Mol. Microbiol.*, 30:674–676, 1998.
Chen et al, *Nat. Biotechnol.*, 19:537–542, 2001.
Crameri et al., *Nat. Biotechnol.*, 14:315–319, 1996.
Cristobal et al., *EMBO J.*, 18:2982–2990, 1999.
Danese and Silhavy, *Annu. Rev. Genet.*, 32:59–94, 1998.
DeLisa et al., *J. Biol. Chem.*, 277(33):29825–29831, 2002.
Feilmeier et al., *J. Bacteriol.*, 182:4068–4076, 2000.
Fromant et al., *Anal. Biochem.*, 224:347–353, 1995.
Georgiou and Valax, *Curr. Opin. Biotechnol.*, 7(2):190–197, 1996.
Guzman et al., *J. Bacteriol.*, 177:4121–4130, 1995.
Hockney, *Trends Biotechnol.*, 12(11):456–463, 1994.
Kaback, *Methods Enzymol.*, 22:99–120, 1971.
Karzai et al., *Nat. Struct. Biol.*, 7:449–455, 2000.
Meyer et al., *Nature*, 297:647–650, 1982.
Nielsen et al., *Magn. Reson. Med.*, 37(2):285–291, 1997.
Pugsley, *Microbiol. Rev.*, 57:50–108, 1993.
Sambrook et al., Molecular Cloning: A Laboratory Manual, 3 ed. Cold Spring Harbor Laboratory Press, Cold Spring Harbor, N.Y., 2000.
Samuelson et al., *Nature*, 406:637–641, 2000.
Santini et al., *J. Biol. Chem.*, 276:8159–8164, 2001.
Sargent et al., *EMBO J.*, 17:3640–3650, 1998.
Sargent et al., *J. Biol. Chem.*, 274:36073–36082, 1999.
Schatz and Dobberstein, *Science*, 271:1519–1526, 1996.
Settles et al., *Science*, 278:1467–1470, 1997.
Stuart and Neupert, *Nature*, 406:575–577, 2000.
Thomas et al., *Mol. Microbiol.*, 39:47–53, 2001.
Weiner et al., *Cell*, 93:93–101, 1998.
Yahr and Wickner, *EMBO J.*, 20:2472–2479, 2001.

What is claimed is:

1. A method of identifying a leader peptide that directs protein export in bacteria, comprising the steps of:
   a) obtaining a library of nucleic acid sequences encoding mutated leader peptides;
   b) constructing a plurality of expression cassettes comprising said nucleic acid sequences encoding mutated leader peptides upstream of a nucleic acid sequence encoding a short-lived reporter protein, wherein said short-lived reporter protein is constructed by operably linking a cytoplasmic degradation sequence to the nucleic acid sequence encoding said reporter protein, wherein the short lived reporter protein is subject to degradation in the cytoplasm of bacteria;
   c) expressing said plurality of expression cassettes in bacteria;
   d) measuring expression of said reporter protein in said bacteria; and
   e) collecting bacteria cells having increased expression of said reporter protein relative to bacteria that do not express a leader peptide that directs protein export of said short lived reporter protein, wherein the mutated leader peptide expressed in said cells that have increased expression of said reporter protein is a leader peptide that directs export from the cytoplasm, whereby said export rescues said short-lived reporter protein from degradation in the cytoplasm.

2. The method of claim 1, wherein said cytoplasmic degradation sequence is selected from the group consisting of SsrA, PEST, sequences recognized by LON, sequences recognized by ClpAP, sequences recognized by ClpXP, sequences recognized by Stsb and sequences recognized by HsIUV.

3. The method of claim 1, wherein said cytoplasmic degradation sequence is attached to the N-terminal or the C-terminal end of said reporter protein.

4. The method of claim 1, wherein said reporter protein is selected from the group consisting of a fluorescent protein, an enzyme, a transport protein, an antibiotic resistance enzyme, a toxin immunity protein, a bacteriophage receptor protein and an antibody.

5. The method of claim 4, wherein said fluorescent protein is green fluorescent protein.

6. The method of claim 1, wherein said nucleic acid sequences encoding mutated leader peptides are generated by a method selected from the group consisting of random mutagenesis, error-prone PCR, site-directed mutagenesis and generation of random DNA fragments.

7. The method of claim 1, wherein said leader peptide mediates protein secretion through a pathway selected from the group consisting of the general secretory (See) pathway, the signal recognition particle (SRP)-dependent pathway, the YidC-dependent pathway and the twin-arginine translocation (Tat) pathway.

8. The method of claim 1, further comprising the steps of:
   f) cloning a selected nucleic acid sequence encoding a mutated leader peptide from collected bacteria cells having increased expression of said reporter protein compared to bacteria cells that express a wild type leader peptide, and
   g) constructing an expression cassette comprising said nucleic acid sequence encoding said mutated selected leader peptide upstream of a nucleic acid sequence encoding a heterologous polypeptide of interest.

9. The method of claim 8, still further comprising expressing said expression cassette in bacteria so that said leader peptide directs increased export of said heterologous polypeptide in bacteria.

10. The method of claim 1, wherein said bacteria are Gram negative bacteria.

11. A method of identifying a leader peptide that directs increased protein export through the Twin Arginine Translocation pathway, comprising the steps of:
    a) generating a library of nucleic acid sequences encoding mutated leader peptides specific for the Twin Arginine Translocation pathway;
    b) constructing a plurality of expression cassettes comprising said nucleic acid sequences encoding mutated leader peptides upstream of a nucleic acid sequence encoding a shaft-lived reporter protein, wherein said short-lived reporter protein is constructed by operably linking a cytoplasmic degradation sequence to the nucleic acid sequence encoding said reporter protein, wherein The short lived reporter protein is subject to degradation in the cytoplasm of bacteria;
    c) expressing said expression cassettes in bacteria;
    d) measuring the expression of said reporter protein in said bacteria; and
    e) collecting bacteria cells having increased expression of said reporter protein relative to bacteria that do not express a peptide leader peptide that directs protein export of said short lived reporter protein, wherein the mutated leader peptide expressed in said cells that exhibit increased expression of said reporter protein is a leader peptide that directs increased protein export from the cytoplasm through the Twin Arginine Translocation pathway, whereby said export rescues said short-lived reporter protein from degradation in the cytoplasm.

12. The method of claim 11, wherein said cytoplasmic degradation sequence is selected from the group consisting of SsrA, PEST, sequences recognized by LON, sequences recognized by ClpAP, sequences recognized by ClpXP, sequences recognized by Stsh and sequences recognized by HsIUV.

13. The method of claim 11, wherein said cytoplasmic degradation sequence is attached to the N-terminal or the C-terminal of said reporter protein.

14. The method of claim 11, wherein said reporter protein is selected from the group consisting of fluorescent protein, an enzyme, a transport protein, an antibiotic resistance enzyme, a toxin immunity protein, a bacteriophage receptor protein and an antibody.

15. The method of claim 14, wherein said fluorescent protein is green fluorescent protein.

16. The method of claim 11, wherein said bacteria are Gram negative bacteria.

17. The method of claim 11, wherein said nucleic acid sequences encoding mutated leader peptides specific for the Twin Arginine Translocation pathway are generated by a method selected from the group consisting of random mutagenesis, error-prone PCR, site-directed mutagenesis and generation of random DNA fragments.

18. The method of claim 11, wherein said leader peptide comprises a sequence selected from the group consisting of SEQ ID NOs:120–128 or a sequence mutated therefrom.

19. A leader peptide that directs increased protein export through the Twin Arginine Translocation pathway, wherein the leader peptide comprises the leader peptide of SEQ ID NO:122.

20. An isolated nucleic acid sequence encoding the leader peptide of claim 19.

* * * * *

UNITED STATES PATENT AND TRADEMARK OFFICE
CERTIFICATE OF CORRECTION

PATENT NO. : 7,419,783 B2  Page 1 of 1
APPLICATION NO. : 10/289135
DATED : September 2, 2008
INVENTOR(S) : George Georgiou et al.

It is certified that error appears in the above-identified patent and that said Letters Patent is hereby corrected as shown below:

In column 1, line 7, delete "60/404,944" and insert --60/404,994-- therefor.

In claim 2, column 89, line 30, delete "CIpAP" and insert --ClpAP-- therefor.

In claim 2, column 89, line 30, delete "CIpXP" and insert --ClXP-- therefor.

In claim 2, column 89, line 31, delete "Stsb" and insert --Stsh-- therefor.

In claim 7, column 89, line 50, delete "See" and insert --Sec-- therefor.

In claim 11, column 90, line 12, delete "shaft" and insert --short-- therefor.

In claim 11, column 90, line 15, delete "The" and insert --the-- therefor.

Signed and Sealed this

Eighteenth Day of November, 2008

JON W. DUDAS
*Director of the United States Patent and Trademark Office*